United States Patent
Sanders et al.

(10) Patent No.: US 12,234,202 B2
(45) Date of Patent: Feb. 25, 2025

(54) COVALENT INHIBITORS OF CORONAVIRUS PAPAIN-LIKE PROTEASE

(71) Applicant: UT-Battelle, LLC, Oak Ridge, TN (US)

(72) Inventors: Brian Sanders, Knoxville, TN (US); Stephanie S. Galanie, Scotch Plains, NJ (US); Jerry M. Parks, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 288 days.

(21) Appl. No.: 17/896,182

(22) Filed: Aug. 26, 2022

(65) Prior Publication Data

US 2023/0102656 A1    Mar. 30, 2023

Related U.S. Application Data

(60) Provisional application No. 63/237,578, filed on Aug. 27, 2021.

(51) Int. Cl.
| | | |
|---|---|---|
| C07C 243/28 | (2006.01) | |
| A61P 31/14 | (2006.01) | |
| C07C 255/03 | (2006.01) | |

(52) U.S. Cl.
CPC ............ *C07C 243/28* (2013.01); *A61P 31/14* (2018.01); *C07C 255/03* (2013.01)

(58) Field of Classification Search
None
See application file for complete search history.

(56) References Cited

U.S. PATENT DOCUMENTS

2011/0269834 A1   11/2011   Ghosh et al.

FOREIGN PATENT DOCUMENTS

WO         02/26697 A2     4/2002

OTHER PUBLICATIONS

Krishnan, S. et al., "Design of Reversible, Cysteine-Targeted Michael Acceptors Guided by Kinetic and Computational Analysis", J. Am. Chem. Soc. 2014, Received May 23, 2014, Published Aug. 25, 2014, pp. 12624-12630, 136 (Year: 2014).*
Ratia, K. et al., "A noncovalent class of papain-like protease/deubiquitinase inhibitors blocks SARS virus replication", PNAS, Oct. 21, 2008, pp. 16119-16124, vol. 105, No. 4 (Year: 2008).*
International Search Report and Written Opinion dated Nov. 4, 2022, issued in PCT/US 22/41629, 8 pages.
Ismail, M.I., et al., "Targeting multiple conformations of SARS-COV2 Papain-Like Protease for drug repositioning: An in-silico study", Computers in Biology and Medicine (2021), Received Dec. 24, 2020, Received in revised form Feb. 15, 2021, Accepted Feb. 19, 2021, Available online Feb. 24, 2021, pp. 1-10, 131, 104295.
Pubchem, SID 396181678, https://pubchem.ncbi.nlm.nih.gov/substance/396181678, Deposited on Dec. 6, 2019, 5 pages.
Baez-Santos, Y.M., et al., "X-ray Structural and Biological Evaluation of a Series of Potent and Highly Selective Inhibitors of Human Coronavirus Papain-like Proteases", J. Med. Chem. 2014, Received Nov. 6, 2013, Published Feb. 25, 2014, pp. 2393-2412, 57.
Ghosh, A.K., et al., "Severe Acute Respiratory Syndrome Coronavirus Papain-like Novel Protease Inhibitors: Design, Synthesis, Protein-Ligand X-ray Structure and Biological Evaluation", J. Med. Chem. 2010, Received Apr. 12, 2010, Published on Web Jun. 9, 2010, pp. 4968-4979, 53.
Krishnan, S., et al., "Design of Reversible, Cysteine-Targeted Michael Acceptors Guided by Kinetic and Computational Analysis", J. Am. Chem. Soc. 2014, Received May 23, 2014, Published Aug. 25, 2014, pp. 12624-12630, 136.
Ratia, K., et al., "A noncovalent class of papain-like protease/deubiquitinase inhibitors blocks SARS virus replication", PNAS, Oct. 21, 2008, pp. 16119-16124, vol. 105, No. 42.
Rut, W., et al., "Activity profiling and crystal structures of inhibitor-bound SARS-COV-2 papain-like protease: A framework for anti-COVID-19 drug design", Sci. Adv. 2020, Oct. 16, 2020, pp. 1-12, 6 (42), eabd4596.

*Primary Examiner* — Samantha L Shterengarts
*Assistant Examiner* — Jed A Kucharczk
(74) *Attorney, Agent, or Firm* — Scully, Scott. Murphy & Presser, P.C.

(57) ABSTRACT

A compound having the following structure:

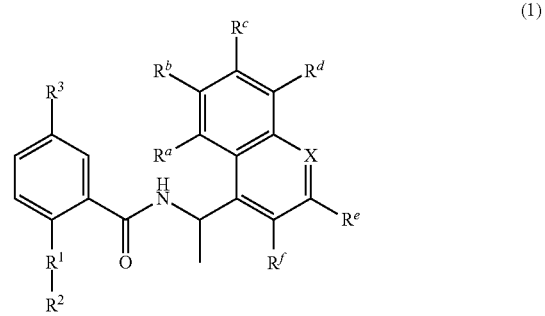

(1)

wherein: $R^1$ is a linker having the formula $-(CH_2)_n-L^1-$, wherein $L^1$ contains 1-6 carbon atoms and at least one $-NH-$ linkage and at least one oxygen-containing or sulfur-containing linkage, and n is an integer of 0-3; $R^2$ is a group having the formula $-C(Y)-E$, wherein Y is O or S, and E is a hydrocarbon group and either: (i) at least one carbon-carbon or carbon-nitrogen unsaturated bond or (ii) at least one alkyl halide group; $R^3$ is selected from H, $NR'_2$, $NHC(O)R'$, and $-(CH_2)_p-T$, wherein T contains at least one $-NH-$ linkage; $R^a$, $R^b$, $R^c$, $R^d$, $R^e$, and $R^f$ are independently selected from of H, hydrocarbon groups containing 1-3 carbon atoms, fluorine atom, and chlorine atom; X is N or $CR^9$, wherein $R^9$ is selected from H, hydrocarbon groups containing 1-3 carbon atoms, fluorine atom, and chlorine atom; and pharmaceutically acceptable salts thereof.

26 Claims, 7 Drawing Sheets
(4 of 7 Drawing Sheet(s) Filed in Color)

(56) References Cited

OTHER PUBLICATIONS

Shen, Z., et al., "Design of SARS-COV-2 PLpro Inhibitors for COVID-19 Antiviral Therapy Leveraging Binding Cooperativity", J. Med. Chem. 2022, Special Issue: COVID-19, Received Jul. 26, 2021, Published Oct. 19, 2021, pp. 2940-2955, 65.

* cited by examiner

COVALENT INHIBITORS OF CORONAVIRUS PAPAIN-LIKE PROTEASE

CROSS REFERENCE TO RELATED APPLICATION

The present application claims benefit of U.S. Provisional Application No. 63/237,578, filed on Aug. 27, 2021, all of the contents of which are incorporated herein by reference.

STATEMENT REGARDING FEDERALLY SPONSORED RESEARCH

This invention was made with government support under Prime Contract No. DE-AC05-00OR22725 awarded by the U.S. Department of Energy. The government has certain rights in the invention.

FIELD OF THE INVENTION

The present invention generally relates to inhibitors of coronavirus papain-like protease, and more particularly, wherein the inhibitors are naphthalene-containing benzamide compounds. The present invention also relates to the use of such inhibitors for inhibiting papain-like protease activity in a subject, or more particularly, treating coronavirus infection in a subject.

BACKGROUND OF THE INVENTION

Severe acute respiratory syndrome coronavirus 2 (SARS-CoV-2) causes COVID-19, which has led to a global pandemic. The virus is highly transmissible and leads to severe, and in many cases life-threatening, respiratory disease with an overall case fatality rate of 2.1% as of August 2021. Few effective drugs have been developed to date, with molnupiravir, nirmatrelvir, and ritonavir being the only currently available oral antivirals for treating SARS-CoV-2 infections. Although recently developed vaccines can be highly effective in preventing COVID-19 or reducing its severity, the emergence of variant strains limits their effectiveness. In addition, vaccines are not yet widely available worldwide, many are unwilling to receive them, and others, despite having received the vaccine, may still contract the disease in breakthrough COVID cases. Efforts to repurpose existing drugs have been largely ineffective, and few effective pharmaceutical treatments have been identified to date. Thus, there is an urgent need to develop new direct-acting antiviral therapeutics that are effective against SARS-CoV-2 and future coronaviruses.

SUMMARY OF THE INVENTION

In a first aspect, the present disclosure is directed to covalent inhibitor molecules of coronavirus papain-like protease (PLpro). The covalent inhibitor molecules are substituted (R)—N-(1-(naphthalen-1-yl)ethyl)benzamide compounds having the following structure:

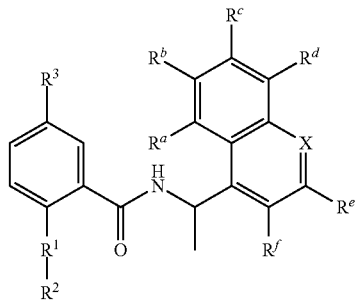

(1)

wherein: $R^1$ is a linker having the formula —$(CH_2)_n$-$L^1$-, wherein $L^1$ contains 1-6 carbon atoms and at least one —NH— linkage and at least one oxygen-containing or sulfur-containing linkage, and n is an integer of 0-3; $R^2$ is a group having the formula —C(Y)-E, wherein Y is O or S, and E is a hydrocarbon group containing 1-12 carbon atoms and either: (i) at least one carbon-carbon or carbon-nitrogen unsaturated bond or (ii) at least one alkyl halide group; $R^3$ is selected from the group consisting of H, $NR'_2$, NHC(O)R', and —$(CH_2)_p$-T, wherein T contains at least one —NH— linkage; R' is independently selected from H and hydrocarbon groups containing 1-6 carbon atoms; and p is a integer of 0-3; $R^a$, $R^b$, $R^c$, $R^d$, $R^e$, and $R^f$ are independently selected from the group consisting of H, hydrocarbon groups containing 1-3 carbon atoms, fluorine atom, and chlorine atom; X is N or $CR^9$, wherein $R^9$ is selected from the group consisting of H, hydrocarbon groups containing 1-3 carbon atoms, fluorine atom, and chlorine atom; and pharmaceutically acceptable salts thereof, specific enantiomers thereof, and racemic mixtures thereof.

The covalent inhibitor molecules having the above generic structural Formula (1) include a linker ($R^1$) and electrophilic warhead ($R^2$) to make them potent covalent PLpro inhibitors. The above linker design provides an enhanced potency in several ways, as follows: (i) it mimics the glycine-glycine linkage of native protein substrates but does not participate in standard amide cleavage chemistry; (ii) it is a narrow linker that occupies minimal steric space, which permits it to fit into the narrow substrate binding cleft of the PLpro enzyme; (iii) the linker contains hydrogen bond donors and acceptors that interact with the enzyme; (iv) the linker terminates with a reactive electrophilic group, placing it near the catalytic cysteine in the active site, Cys111, and allowing for covalent bond formation; and (v) the presence of functional groups in the $R^3$ position mimic positively charged arginine or lysine residues of the native substrate sequence and enhance efficacy.

In particular embodiments, the covalent inhibitor molecules have any of the following more specific structures:

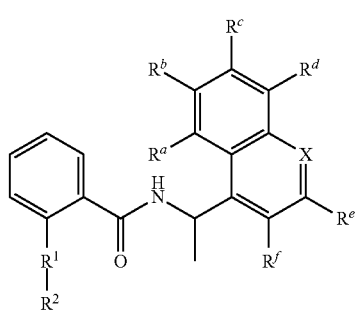

(1a)

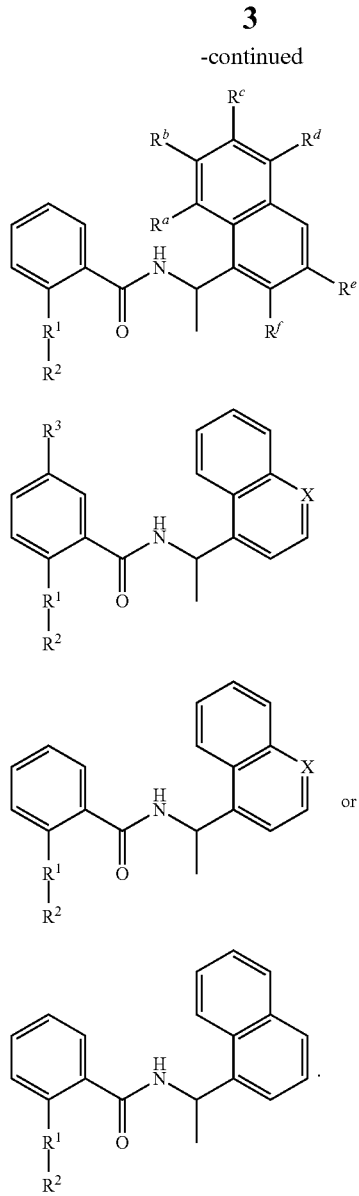

In another aspect, the present disclosure is directed to a method for inhibiting papain-like protease (PLpro) activity in a subject, the method comprising administering a therapeutically effective dosage of a compound of Formula (1) or any sub-formula thereof or particular compound thereof to the subject to result in inhibition of PLpro activity in the subject. In more particular embodiments, the method is directed to treating coronavirus infection in a subject, the method comprising administering a therapeutically effective dosage of a compound of Formula (1) or any sub-formula thereof or particular compound thereof to the subject to result in inhibition or prevention of one or more coronavirus symptoms in the subject.

BRIEF DESCRIPTION OF THE DRAWINGS

The patent or application file contains at least three drawings executed in color. Copies of this patent or patent application publication with color drawing(s) will be provided by the Office.

FIG. 2A shows the structure and domains of PLpro from SARS-CoV-2 (PDB entry 7JIR). Selected features are labeled. FIG. 2B shows interactions between PLpro and the noncovalent inhibitor GRL0617.

FIG. 5A presents data from a fluorogenic peptide activity assay after 30-min preincubation with compound 7. Data points are the average of n=2 independent samples±range and are representative of n=3 independent experiments. IC$_{50}$ is the concentration at which 50% inhibition was observed, and bracketed values are the 95% confidence interval. Curve is the non-linear regression to the normalized inhibitor dose response equation. FIG. 5B presents time-dependent characterization with a fluorogenic peptide assay. Data points are $k_{obs}$ values determined by fitting the exponential decay equation to initial rates determined at various inhibitor concentrations and preincubation times, normalized to no preincubation. $k_{obs}$ values were determined from n=2 independent experiments with n=2 independent samples each ±95% confidence interval of the nonlinear regression. Line represents the linear regression yielding as its slope the second-order rate constant ($k_{inact}/K_I$). FIG. 5C presents intact protein ESI-MS spectra of PLpro (black) and PLpro incubated with 7 (red); a.i., arbitrary intensity; m/z, mass-to-charge ratio. FIG. 5D presents percent viability of Vero E6 cells after 48 h following pretreatment with 7 (black squares), pretreatment with 7 and infection with SARS-CoV-2 (red circles), or pretreatment with remdesivir and infected with SARS-CoV-2 (blue triangles). Data points are the average of n=2 independent samples±range and are representative of n=2 independent experiments. EC$_{50}$ is the concentration at which 50% effect was observed and bracketed values are the 95% confidence interval. Curves are non-linear regressions to the normalized dose response equation.

FIG. 6A shows anti-HA beads after immunoprecipitation and whole cell lysates probed with anti-HA antibody. The asterisk indicates IgG heavy and light chains. Anti-HA beads were assayed for Nsp3 deISGylase activity using an ISG15-CHOP2 assay in the presence of the dose range of compound 7 (FIG. 6B) or GRL0617 (FIG. 6C).

FIG. 7A shows overall structure and interactions between the active site residues and 7 (cyan sticks). The electron density for 7 is shown in blue mesh (Fo-Fc omit map contoured at 1.5 σ). FIG. 7B shows superposition of the covalently docked model of 7 (grey sticks) and the co-crystal structure of PLpro and 7 (cyan sticks). FIG. 7C shows structural basis for selectivity toward PLpro. Superposition of 7 bound to PLpro onto human deubiquitinase UCHL1 (PDB entry 3KW5). The crossover loop of UCHL1, 153-RVDDK-157, covers the narrow groove and blocks the naphthylmethylamine core of 7 from binding. The crossover loop is longer and, in some cases, more disordered in UCHL3 and UCHL5. FIG. 7D shows superposition of 7 bound to PLpro onto human USP4 (PDB entry 2Y6E). Severe steric clashes are present between the naphthyl ring of 7 and Phe828 and Lys838 of USP4 (light pink sticks), both of which are conserved in 80% of human USPs.

DETAILED DESCRIPTION OF THE INVENTION

Figure 1:
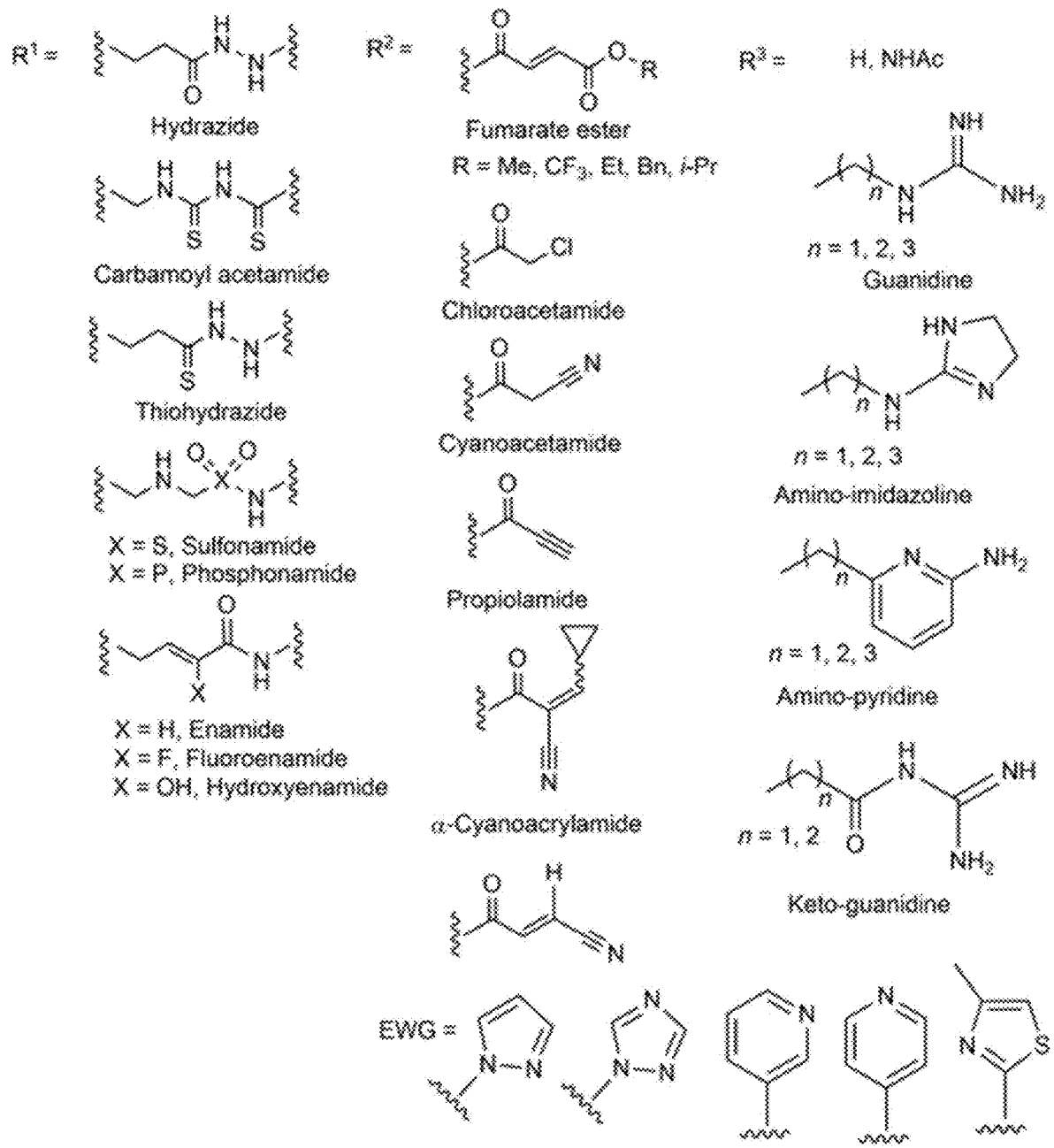
FIG. 1 shows examples of peptidomimetic linkers, electrophilic groups, and arginine mimics for variable groups $R^1$, $R^2$, and $R^3$.

As used herein, the term "hydrocarbon group" (also denoted by the group R) is defined as a chemical group containing at least carbon and hydrogen atoms. In some embodiments, R is composed solely of carbon and hydrogen, except that the hydrocarbon group may (i.e., optionally) be substituted with one or more fluorine atoms to result in partial or complete fluorination of the hydrocarbon group. In different embodiments, one or more of the hydrocarbon groups contain, for example, 1, 2, 3, 4, 5, 6, 7, 8, 9, 10, 11, or 12 carbon atoms, or a number of carbon atoms within a particular range bounded by any two of the foregoing carbon numbers (e.g., 1-12, 1-8, 1-6, 1-5, 1-4, 1-3, 2-12, 2-8, 2-6, 2-5, 2-4, or 2-3 carbon atoms). Hydrocarbon groups in different compounds described herein, or in different generic groups of a compound, may possess the same or different number (or preferred range thereof) of carbon atoms. For example, as further discussed below, any one of $R^1$, $R^2$, and $R^3$ in any of the generic formulas disclosed herein may independently contain a number of carbon atoms within any of the ranges provided above.

In a first set of embodiments, the hydrocarbon group (R) is a saturated and straight-chained group, i.e., a straight-chained (linear) alkyl group. Some examples of straight-chained alkyl groups include methyl, ethyl, n-propyl, n-butyl, n-pentyl, n-hexyl, n-heptyl, n-octyl, n-nonyl, n-decyl, n-undecyl, and n-dodecyl groups.

In a second set of embodiments, the hydrocarbon group (R) is saturated and branched, i.e., a branched alkyl group. Some examples of branched alkyl groups include isopropyl (2-propyl), isobutyl (2-methylprop-1-yl), sec-butyl (2-butyl), t-butyl (1,1-dimethylethyl-1-yl), 2-pentyl, 3-pentyl, 2-methylbut-1-yl, isopentyl (3-methylbut-1-yl), 1,2-dimethylprop-1-yl, 1,1-dimethylprop-1-yl, neopentyl (2,2-dimethylprop-1-yl), 2-hexyl, 3-hexyl, 2-methylpent-1-yl, 3-methylpent-1-yl, isohexyl (4-methylpent-1-yl), 1,1-dimethylbut-1-yl, 1,2-dimethylbut-1-yl, 2,2-dimethylbut-1-yl, 2,3-dimethylbut-1-yl, 3,3-dimethylbut-1-yl, 1,1,2-trimethylprop-1-yl, 1,2,2-trimethylprop-1-yl groups, isoheptyl, isooctyl, and the numerous other branched alkyl groups having up to 12 carbon atoms, wherein the "1-yl" suffix represents the point of attachment of the group.

In a third set of embodiments, the hydrocarbon group (R) is saturated and cyclic, i.e., a cycloalkyl group. Some examples of cycloalkyl groups include cyclopropyl, cyclobutyl, cyclopentyl, cyclohexyl, cycloheptyl, and cyclooctyl groups. The cycloalkyl group can also be a polycyclic (e.g., bicyclic) group by either possessing a bond between two ring groups (e.g., dicyclohexyl) or a shared (i.e., fused) side (e.g., decalin and norbornane).

In a fourth set of embodiments, the hydrocarbon group (R) is unsaturated and straight-chained, i.e., a straight-chained (linear) olefinic or alkenyl group. The unsaturation occurs by the presence of one or more carbon-carbon double bonds and/or one or more carbon-carbon triple bonds. Some examples of straight-chained olefinic groups include vinyl, propen-1-yl (allyl), 3-buten-1-yl ($CH_2$=CH—$CH_2$—$CH_2$—), 2-buten-1-yl ($CH_2$—CH=CH—$CH_2$—), butadienyl, 4-penten-1-yl, 3-penten-1-yl, 2-penten-1-yl, 2,4-pentadien-1-yl, 5-hexen-1-yl, 4-hexen-1-yl, 3-hexen-1-yl, 3,5-hexadien-1-yl, 1,3,5-hexatrien-1-yl, 6-hepten-1-yl, ethynyl, propargyl (2-propynyl), 3-butynyl, and the numerous other straight-chained alkenyl or alkynyl groups having up to 12 carbon atoms.

In a fifth set of embodiments, the hydrocarbon group (R) is unsaturated and branched, i.e., a branched olefinic or alkenyl group. Some examples of branched olefinic groups include propen-2-yl ($CH_2$=C·—$CH_3$), 1-buten-2-yl ($CH_2$=C·—$CH_2$—$CH_3$), 1-buten-3-yl ($CH_2$=CH—CH·—$CH_3$), 1-propen-2-methyl-3-yl ($CH_2$=C($CH_3$)—$CH_2$—), 1-penten-4-yl, 1-penten-3-yl, 1-penten-2-yl, 2-penten-2-yl, 2-penten-3-yl, 2-penten-4-yl, and 1,4-pentadien-3-yl, and the numerous other branched alkenyl groups having up to 12 carbon atoms, wherein the dot in any of the foregoing groups indicates a point of attachment.

In a sixth set of embodiments, the hydrocarbon group (R) is unsaturated and cyclic, i.e., a cycloalkenyl group. The unsaturated cyclic group can be aromatic or aliphatic. Some examples of unsaturated cyclic hydrocarbon groups include cyclopropenyl, cyclobutenyl, cyclopentenyl, cyclopentadienyl, cyclohexenyl, cyclohexadienyl, phenyl, benzyl, cycloheptenyl, cycloheptadienyl, cyclooctenyl, cyclooctadienyl, and cyclooctatetraenyl groups. The unsaturated cyclic hydrocarbon group may or may not also be a polycyclic group (such as a bicyclic or tricyclic polyaromatic group) by either possessing a bond between two of the ring groups (e.g., biphenyl) or a shared (i.e., fused) side, as in naphthalene, anthracene, phenanthrene, phenalene, or indene fused ring systems. All of the foregoing cyclic groups are carbocyclic groups.

Notably, the term "hydrocarbon group" also includes "hydrocarbon linkers." Hydrocarbon linkers may be denoted by "L," such as $L^1$ or $L^2$, or by an R group (e.g., $R^1$) connected to other groups by two separate bonds, such as —$R^1$—, as depicted in Formula (1). A hydrocarbon linker can be derived from any of the hydrocarbon groups described above by removing a hydrogen atom from the hydrocarbon group. For example, a hydrogen atom may be removed from an ethyl group (—$CH_2CH_3$) to result in an ethylene (—$CH_2CH_2$—) linker. Linkers disclosed in this application (e.g., $L^1$ and $R^1$) may independently have any of the carbon numbers provided above and may be derived from any of the linear or branched alkyl, alkenyl, or alkynyl groups described above or saturated or unsaturated cyclic groups described above. The linker may also optionally include one or more heteroatoms, as described below.

One or more of the hydrocarbon groups (R) or linkers thereof may also include one or more heteroatoms (i.e., non-carbon and non-hydrogen atoms), such as one or more heteroatoms selected from oxygen, nitrogen, sulfur, silicon, phosphorus, boron, and halide atoms, as well as groups containing one or more of these heteroatoms (i.e., heteroatom-containing groups). Some examples of oxygen-containing groups include hydroxy (OH), alkoxy (OR'), carbonyl-containing (e.g., carboxylic acid, ketone, aldehyde, carboxylic ester, amide, and urea functionalities), nitro (NO$_2$), carbon-oxygen-carbon (ether), sulfonyl, and sulfinyl (i.e., sulfoxide) groups. Some particular examples of alkoxy groups —OR' include methoxy, ethoxy, n-propoxy, isopropoxy, n-butoxy, isobutoxy, t-butoxy, phenoxy, benzyloxy, 2-hydroxyethoxy, 2-methoxyethoxy, 2-ethoxyethoxy, vinyloxy, and allyloxy groups. In the case of an ether group, the ether group can also be a polyalkyleneoxide (polyalkyleneglycol) group, such as a polyethyleneoxide group. Some examples of nitrogen-containing groups include primary amine, secondary amine, tertiary amine (i.e., —NR$_2$ or NR$_3^+$, wherein R is independently selected from H and hydrocarbon groups set forth above), nitrile, amide (i.e., —C(O)NR$_2$ or —NRC(O)R, wherein R is independently selected from hydrogen atom and hydrocarbon groups set forth above), imine (e.g., —CR=NR, wherein R is independently H or a hydrocarbon group), oxime (—CR=N—OH), amidoxime (—C(NH$_2$)=N—OH), nitro, urea (—NR—C(O)—NR$_2$, wherein R is independently H or a hydrocarbon group), and carbamate groups (—NR—C(O)—OR, wherein R is independently H or a hydrocarbon group). Some examples of phosphorus-containing groups include —PR$_2$, —PR$_3$+, —P(=O)R$_2$, —P(OR)$_2$, —O—P(OR)$_2$, —R—P(OR)$_2$, —P(=O)(OR)$_2$, —O—P(=O)(OR)$_2$, —O—P(=O)(OR)(R), —O—P(=O)R$_2$, —R—P(=O)(OR)$_2$, —R—P(=O)(OR)(R), and —R—P(=O)R$_2$ groups, wherein R is independently selected from hydrogen atom and hydrocarbon groups set forth above. Some examples of sulfur-containing groups include mercapto (i.e., —SH), thioether (i.e., sulfide, e.g., —SR), disulfide (—R—S—S—R), sulfoxide (—S(O)R), sulfone (—SO$_2$R), sulfonate (—S(=O)$_2$OR, wherein R is H, a hydrocarbon group, or a cationic group), and sulfate groups (—OS(=O)$_2$OR, wherein R is H, a hydrocarbon group, or a cationic group). Some examples of halide atoms include fluorine, chlorine, bromine, and iodine.

One or more of the heteroatoms described above (e.g., oxygen, nitrogen, and/or sulfur atoms) can be inserted between carbon atoms (e.g., as —O—, —NH—, or —S—) in any of the hydrocarbon groups or linkers described above to form a heteroatom-substituted hydrocarbon group or linker. Alternatively, or in addition, one or more of the heteroatom-containing groups can replace one or more hydrogen atoms on the hydrocarbon group or linker. In some embodiments, one or more of the above described heteroatoms or heteroatom-containing groups are excluded from R or a linker thereof.

In some embodiments, the hydrocarbon group is or includes a cyclic or polycyclic group that includes at least one ring heteroatom (for example, one, two, three, four, or higher number of heteroatoms). Such ring heteroatom-substituted cyclic groups are referred to herein as "heterocyclic groups." As used herein, a "ring heteroatom" is an atom other than carbon and hydrogen (typically, selected from nitrogen, oxygen, and sulfur) that is inserted into, or replaces a ring carbon atom in, a hydrocarbon ring structure. In some embodiments, the heterocyclic group is saturated, while in other embodiments, the heterocyclic group is unsaturated (i.e., aliphatic or aromatic heterocyclic groups, wherein the aromatic heterocyclic group is also referred to herein as a "heteroaromatic ring," or a "heteroaromatic fused-ring system" in the case of at least two fused rings, at least one of which contains at least one ring heteroatom). In some embodiments, the heterocyclic group is bound via one of its ring carbon atoms to another group (i.e., other than hydrogen atom and adjacent ring atoms), while the one or more ring heteroatoms are not bound to another group. In other embodiments, the heterocyclic group is bound via one of its heteroatoms to another group, while ring carbon atoms may or may not be bound to another group.

Some examples of saturated heterocyclic groups include those containing at least one oxygen atom (e.g., oxetane, tetrahydrofuran, tetrahydropyran, 1,4-dioxane, 1,3-dioxane, and 1,3-dioxepane rings), those containing at least one nitrogen atom (e.g., pyrrolidine, piperidine, piperazine, imidazolidine, azepane, and decahydroquinoline rings), those containing at least one sulfur atom (e.g., tetrahydrothiophene, tetrahydrothiopyran, 1,4-dithiane, 1,3-dithiane, and 1,3-dithiolane rings), those containing at least one oxygen atom and at least one nitrogen atom (e.g., morpholine and oxazolidine rings), those containing at least one oxygen atom and at least one sulfur atom (e.g., 1,4-thioxane), and those containing at least one nitrogen atom and at least one sulfur atom (e.g., thiazolidine and thiamorpholine rings).

Some examples of unsaturated heterocyclic groups include those containing at least one oxygen atom (e.g., furan, pyran, 1,4-dioxin, and dibenzodioxin rings), those containing at least one nitrogen atom (e.g., pyrrole, imidazole, pyrazole, pyridine, pyrazine, pyrimidine, 1,3,5-triazine, azepine, diazepine, indole, purine, benzimidazole, indazole, 2,2'-bipyridine, quinoline, isoquinoline, phenanthroline, quinoxaline, quinazoline, pyridazine, and cinnoline), those containing at least one sulfur atom (e.g., thiophene, thianaphthene, and benzothiophene rings), those containing at least one oxygen atom and at least one nitrogen atom (e.g., oxazole, isoxazole, benzoxazole, benzisoxazole, and oxazoline rings), and those containing at least one nitrogen atom and at least one sulfur atom (e.g., thiazole, isothiazole, benzothiazole, benzoisothiazole, and thiazoline rings).

In a first aspect, the present disclosure is directed to covalent inhibitor molecules of coronavirus papain-like protease (PLpro) having the following structure:

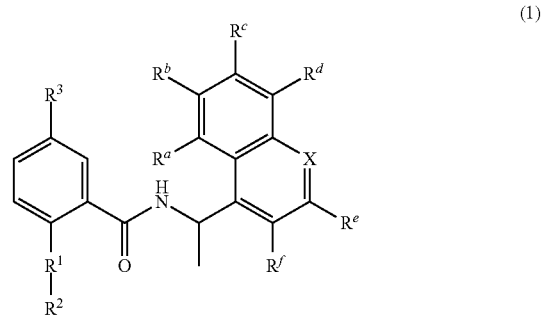

(1)

The variable R$^1$ in Formula (1) is a linker having a peptidomimetic design and having the formula —(CH$_2$)$_n$-L$^1$-, wherein L$^1$ contains 1-6 carbon atoms and at least one —NH— linkage and at least one oxygen-containing or sulfur-containing linkage, and n is an integer of 0, 1, 2, or 3 or an integer within a range bounded by any two of these values (e.g., 0-3, 0-2, 1-2, 1-3, or 2-3). Some examples of oxygen-containing linkages include carbonyl (—C(O)—), sulfonyl (—SO$_2$—), sulfoxide (—S(O)—), phosphinyl (—PO$_2$—), hydroxy-containing (e.g., —CH(OH)—), and ether-containing (e.g., —CH$_2$—O—CH$_2$—) linkages. In some embodiments, the oxygen-containing linkage contains at least one unsaturated oxygen, such as a carbonyl, sulfonyl, sulfoxide, or phosphinyl linker. Some examples of sulfur-containing linkages include thiocarbonyl (—C(S)—), thiol-containing (e.g., —CH(SH)—), and thioether-containing (e.g., —CH$_2$—S—CH$_2$—) linkages. In some embodiments, the sulfur-containing linkage contains at least one unsaturated oxygen, such as a thiocarbonyl, thiol-containing, or thioether-containing linker. In some embodiments, L$^1$ contains a single —NH— linker. In other embodiments, L$^1$ contains two or more —NH— linkers. In the case of L$^1$ containing two or more —NH— linkers, two of the —NH— linkers may be bonded to form a hydrazidyl, hydrazonyl, or azo linkage.

In some embodiments, the —NH-containing linkage in R$^1$ is spaced apart from (not connected with), the oxygen-containing or sulfur-containing linkage. Some examples of R$^1$ containing an —NH-containing linkage spaced apart from an oxygen-containing or sulfur-containing linkage include —(CH$_2$)$_{1,2,3}$—NH—(CH$_2$)$_{1,2,3}$—C(O or S))—, —(CH$_2$)$_{1,2,3}$—C(O or S)—(CH$_2$)$_{1,2,3}$—NH—, —(CH$_2$)$_{1,2,3}$—NH—(CH$_2$)$_{1,2,3}$—C(O or S))—NH—, —(CH$_2$)$_{1,2,3}$NH—NH—(CH$_2$)$_{1,2,3}$—C(O or S))—, —(CH$_2$)$_{1,2,3}$N=N—(CH$_2$)$_{1,2,3}$—C(O or S))—, —(CH$_2$)$_{1,2,3}$NH—NH—(CH$_2$)$_{1,2,3}$—C(O or S))—NH—, —(CH$_2$)$_{1,2,3}$—C(O or S)—(CH$_2$)$_{1,2,3}$—NH—, —(CH$_2$)$_{1,2,3}$—C(O or S)—(CH$_2$)$_{1,2,3}$—NH—NH—, —(CH$_2$)$_{1,2,3}$—C(O or S)—(CH$_2$)$_{1,2,3}$N=N, —(CH$_2$)$_{1,2,3}$—C(O or S)—(CH$_2$)$_{1,2,3}$—NH—N=, —(CH$_2$)$_{1,2,3}$—C(O or S)—(CH$_2$)$_{0,1,2,3}$CH=N—NH—, —(CH$_2$)$_{1,2,3}$—NH—(CH$_2$)$_{1,2,3}$—S(O$_2$)—NH—, and —(CH$_2$)$_{1,2,3}$—NH—(CH$_2$)$_{1,2,3}$—P(O$_2$)—NH, In other embodiments, the —NH-containing linkage in R$^1$ is connected to the oxygen-containing or sulfur-containing linkage to result in, for example, a hydrazide, thiohydrazide, carbamoyl acetamide, carbamothioyl acetamide, sulfonamide, phosphonamide, enamide, sulfonylurea, or phosphinylamide that covalently connects to R$^2$. Some examples of R$^1$ containing an —NH-containing linkage connected to an oxygen-containing or sulfur-containing linkage include —(CH$_2$)$_{1,2,3}$—C(O or S)—NH—, —(CH$_2$)$_{1,2,3}$—C(O or S)—NH—NH—, —(CH$_2$)$_{1,2,3}$—C(O or S)—NH—N=, —(CH$_2$)$_{1,2,3}$—C(O or S)—N=N—, —(CH$_2$)$_{1,2,3}$—NH—C(O or S)—, —(CH$_2$)$_{1,2,3}$—NH—NH—C(O or S)—, —(CH$_2$)$_{1,2,3}$—N=N—C(O or S)—, (CH$_2$)$_{0,1,2,3}$CH=N—NH—C(O or S)—, —(CH$_2$)$_{1,2,3}$—NH—C(O or S)—NH—, —(CH$_2$)$_{1,2,3}$—NH—C(O or S)—NH—NH—, —(CH$_2$)$_{1,2,3}$—NH—C(O or S)—NH—C(O)—, and —(CH$_2$)$_{1,2,3}$—(C=C)—C(OH)—C(O or S)—NH.

The variable R$^2$ in Formula (1) is an electrophilic group having the formula —C(Y)-E, wherein Y is O or S, and E is a hydrocarbon group containing 1-12 carbon atoms and either: (i) at least one carbon-carbon or carbon-nitrogen unsaturated bond or (ii) at least one alkyl halide group. The carbon-carbon unsaturated bond may be a carbon-carbon double bond or triple bond, which may a linking bond (e.g., —CH=CH— or —C≡C—) or alkenyl or alkynyl group (e.g., —CH=CH$_2$ or —C≡CH). The carbon-nitrogen unsaturated bond may be a —C=N-linking bond or a nitrile (—CN) group.

In particular embodiments where E contains at least one carbon-carbon or carbon-nitrogen unsaturated bond, E may more particularly have the formula —(C=C)—C(O)O—V, in which case R$^2$ has the formula —C(Y)—(C=C)—C(O)O—V, wherein Y is O or S, and V is a hydrocarbon group containing 1-12 carbon atoms, optionally substituted with one or more F atoms. In a first set of embodiments, V is a linear, branched, or cyclic alkyl, alkenyl, or alkynyl hydrocarbon group containing 1, 2, 3, 4, 5, or 6 carbon atoms (e.g., 1-6, 1-4, 1-3, or 3-6 carbon atoms), such as any of those described earlier above, methyl, fluoromethyl, difluoromethyl, trifluoromethyl, ethyl, 2,2,2-trifluoroethyl, perfluoroethyl, n-propyl, isopropyl, cyclopropyl, n-butyl, isobutyl, sec-butyl, t-butyl, cyclobutyl, n-pentyl, isopentyl, neopentyl, cyclopentyl, n-hexyl, isohexyl, 3,3-dimethylbutyl, cyclohexyl, and phenyl). In some embodiments, V is a hydrocarbon group containing 7, 8, 9, 10, 11, or 12 carbon atoms, such as any of those described earlier above, including aromatic rings (e.g., n-heptyl, isoheptyl, n-octyl, isooctyl, benzyl, tolyl, xylyl, mesityl, naphthyl, diphenyl, and norbornyl). In a second set of embodiments, V has the formula —(CH$_2$)$_r$—U, wherein U is a carbocyclic or heterocyclic group and r is an integer of 0, 1, 2, or 3 (e.g., 0-3 or 1-3), and wherein U may be attached to any carbon atom of the linker, such as the terminal carbon. The group U can be selected from any of the carbocyclic or heterocyclic groups described earlier above, including aromatic and heteroaromatic groups described earlier above. In a third set of embodiments, E is a hydrocarbon group containing 1-12 carbon atoms and at least one alkyl halide group, wherein the halide may be F, Cl, Br, or I. In some embodiments, E is an alkyl halide group having the formula —(CH$_2$)$_s$—W, in which case R$^2$ has the overall formula —C(Y)—(CH$_2$)$_s$—W, wherein W is halogen (F, Cl, Br, or I) and subscript s is 0, 1, 2, or 3 (e.g., 0-3, 1-2, or 1-3) and wherein W may be attached to any carbon atom of the linker, such as the terminal carbon. In a fourth set of embodiments, E is a hydrocarbon group containing 1-12 carbon atoms and at least one nitrile group. In some embodiments, E is an alkyl nitrile group having the formula —(CH$_2$)$_s$—CN, in which case R$^2$ has the overall formula —C(Y)—(CH$_2$)$_s$—CN, wherein subscript s is 0, 1, 2, or 3 (e.g., 0-3, 1-2, or 1-3) and wherein CN may be attached to any carbon atom of the linker, such as the terminal carbon.

In some embodiments, R$^2$ represents an electrophilic functional group and is selected from —C(O)—(C=C)—C(O)—O—X, where X can be —CH$_3$, —CF$_3$, —CH$_2$—CH$_3$, —CH$_2$—Y, where Y=aromatic ring, e.g., C$_6$H$_5$ or 5- and 6-membered heterocycles containing one or more ring heteroatoms selected from N, O, and/or S. In other embodiments, R$^2$ may be —C(O)—(CH$_2$)—Cl, —C(O)—CH$_2$—(C≡N), —C(O)—CH=CH$_2$, or —C(O)—C≡C—X, where X=H, CH$_3$, —CH$_2$—C$_6$H$_5$ aromatic. In other embodiments, R$^2$ may be —C(O)—C(C≡N)—(C=C)-(E,Z-cyclopropyl). In other embodiments, R$^2$ may be —C(O)—C=C—(C≡N)(EWG), where EWG=electron withdrawing group, such as an aromatic ring, e.g., C$_6$H$_5$ or 5- and 6-membered heterocycles containing one or more ring heteroatoms selected from N, O, and/or S, as described in detail earlier above. In yet other embodiments, R$^2$ electrophilic groups can contain optional substitutions and connectivities leading to substituted fumarate esters, chloroacetamides, cyanoacetamides, substituted acrylamides, substituted propiolamides, substituted alpha-cyanoacrylamides, and substituted acrylonitriles.

The variable R$^3$ in Formula (1) is, in one set of embodiments, hydrogen atom (H).

In some embodiments, R$^3$ represents a substitution of the benzamide region of (R)—N-(1-(naphthalen-1-yl)ethyl)benzamide core intended to generate favorable interactions with solvent water and surrounding amino acids, and in some embodiments, are intended to generate a positively charged group. In more specific embodiments, R$^3$ is selected from —H, —NH$_2$, —NHAc, (CH$_2$)$_{1,2,3}$—NH—C(NH)(NH$_2$), (CH$_2$)$_{1,2,3}$—C(O)—NH—C(NH)(NH$_2$), (CH$_2$)$_{1,2,3}$—NH—X, where X=N-containing heterocycles and substituted N-containing heterocycles that mimic arginine amino acids by generating positively charged groups (e.g., as shown in FIG. 1) that are PIpro inhibitors and are useful for treating SARS-CoV-2 or related coronavirus infections and disease symptoms associated with such viruses.

In another set of embodiments, R³ is NR'₂, wherein R' is independently selected from H and hydrocarbon groups containing 1-6 carbon atoms. In some embodiments, both R' are H atoms, which corresponds to R³ being NH₂. In other embodiments, one R' is H and the other is a hydrocarbon group containing 1-6 carbon atoms. In other embodiments, both R' are hydrocarbon groups containing 1-6 carbon atoms, wherein the hydrocarbon groups may be the same or different. R' may be independently selected from any of the hydrocarbon groups described above containing 1-6 carbon atoms. In particular embodiments, one or both R' are selected from linear or branched alkyl groups containing 1-6 carbon atoms, such as methyl, ethyl, n-propyl, n-butyl, n-pentyl, n-hexyl, isopropyl, isobutyl, sec-butyl, t-butyl, isopentyl, neopentyl, and isohexyl groups.

In another set of embodiments, R³ is NHC(O)R', wherein R' is selected from H and hydrocarbon groups containing 1-6 carbon atoms. In one embodiment, R' is H, which corresponds to R³ being NHC(O)H. In other embodiments, R' is a hydrocarbon group containing 1-6 carbon atoms, wherein the hydrocarbon groups may be the same or different. R' may be selected from any of the hydrocarbon groups described above containing 1-6 carbon atoms. In particular embodiments, R' is selected from linear or branched alkyl groups containing 1-6 carbon atoms, such as methyl, ethyl, n-propyl, n-butyl, n-pentyl, n-hexyl, isopropyl, isobutyl, sec-butyl, t-butyl, isopentyl, neopentyl, and isohexyl groups.

In another set of embodiments, R³ is —(CH₂)$_p$-T, wherein T contains at least one —NH— linkage, and p is an integer of 0-3. In some embodiments, T contains at least one —NH— linkage and a carbonyl (—CO—) linkage, which may be separate or may be combined to form an amide or urea linkage. T typically contains 1, 2, or 3 carbon atoms. In some embodiments, T may be or include a guanidine or guanidinium group. In alternative embodiments, T may include at least one —NH— linkage and a saturated or unsaturated N-containing heterocycle, such as any of those described earlier above.

The variables $R^a$, $R^b$, $R^c$, $R^d$, $R^e$, and $R^f$ in Formula (1) are independently selected from H, hydrocarbon groups containing 1-3 carbon atoms, fluorine atom, and chlorine atom. In some embodiments, $R^a$, $R^b$, $R^c$, $R^d$, $R^e$, and $R^f$ are all hydrogen atoms. In other embodiments, precisely or at least one or two of $R^a$, $R^b$, $R^c$, $R^d$, $R^e$, and $R^f$ are hydrocarbon groups containing 1-3 carbon atoms, such as any of the groups described earlier above. In specific embodiments, the hydrocarbon groups containing 1-3 carbon atoms are selected from, for example, methyl, ethyl, n-propyl, isopropyl, cyclopropyl, and fluorinated versions thereof (e.g., fluoromethyl, difluoromethyl, trifluoromethyl, 2-fluoroethyl, and 2,2,2-trifluoroethyl groups). In other embodiments, precisely or at least one or two of $R^a$, $R^b$, $R^c$, $R^d$, $R^e$, and $R^f$ are selected from fluorine atoms and/or chlorine atoms.

In one embodiment, the variable X is $CR^g$, wherein $R^g$ is selected from H, hydrocarbon groups containing 1-3 carbon atoms, fluorine atom, and chlorine atom. In one embodiment, X is CH. In another embodiment, X is $CR^g$, wherein $R^g$ is a hydrocarbon group containing 1-3 carbon atoms, such as any of the groups described earlier above. In specific embodiments, the hydrocarbon groups containing 1-3 carbon atoms are selected from, for example, methyl, ethyl, n-propyl, isopropyl, cyclopropyl, and fluorinated versions thereof (e.g., fluoromethyl, difluoromethyl, trifluoromethyl, 2-fluoroethyl, and 2,2,2-trifluoroethyl groups). In another embodiment, X is CF or CCl. In another embodiment, the variable X is N, which results in a quinoline ring system.

In one embodiment, the molecule of Formula (1) is a molecule listed in Table 1 below. For example, the molecule of Formula (1) may have R¹=—(CH₂)₂—C(O)—NH—NH—; R²=—C(O)—(C≡C)—C(O)—O—CH₃; R³=H. In another example, the molecule of Formula (1) has R¹=—(CH₂)₂—C(O)—NH—NH; R²=—C(O)—(C≡C)—C(O)—O—CH₃; R³=NHAc. In another example, the molecule of Formula (1) has R¹=—(CH₂)₂—C(O)—NH—NH; R²=—C(O)—(CH₂)—Cl; R³=H. In yet another example, the molecule of Formula (1) has R¹=—(CH₂)₂—C(O)—NH—NH; R²=—C(O) (CH₂) Cl; R₃=NHAc. In a further example, the molecule of Formula (1) has R¹=—(CH₂)₂—C(O)—NH—NH—; R²=C(O)—CH₂—(C≡N); R³=H. In another example, the molecule of Formula (1) has R¹=—(CH₂)₂—C(O)—NH—NH; R²=—C(O)—C≡C—H; R³=H. In an additional example, the molecule of Formula (1) has R¹=—(CH₂)₂—C(O)—NH—NH—; R²=—C(O)—C(C≡N)—(C=C)-(E,Z-cyclopropyl); R³=H. Various possible groups for R¹, R², and R³ are provided in FIG. 1. Any combination of groups provided for R¹, R², and R³ can be used.

In more specific embodiments of Formula (1), the compound has the following structure:

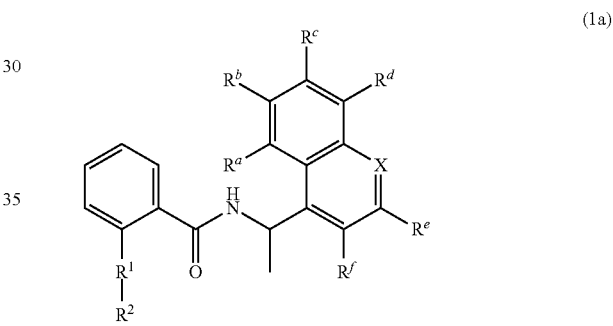

(1a)

wherein R¹, R², X, $R^a$, $R^b$, $R^c$, $R^d$, $R^e$, and $R^f$ are as defined under Formula (1), including all of the possible embodiments and combinations thereof described above under Formula (1).

In other specific embodiments of Formula (1), the compound has the following structure:

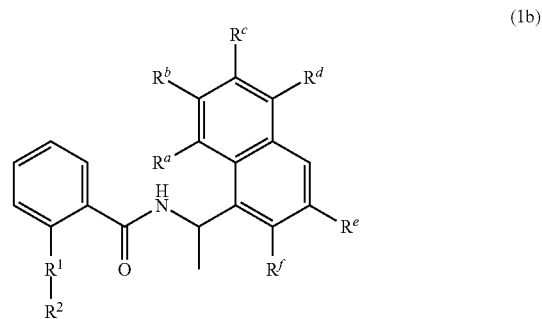

(1b)

wherein R¹, R², $R^a$, $R^b$, $R^c$, $R^d$, $R^e$, and $R^f$ are as defined under Formula (1), including all of the possible embodiments and combinations thereof described above under Formula (1).

In other specific embodiments of Formula (1), the compound has the following structure:

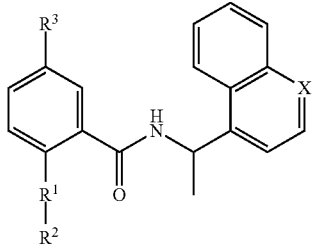

(1c)

wherein $R^1$, $R^2$, $R^3$, and X are as defined under Formula (1), including all of the possible embodiments and combinations thereof described above under Formula (1).

In other specific embodiments of Formula (1), the compound has the following structure:

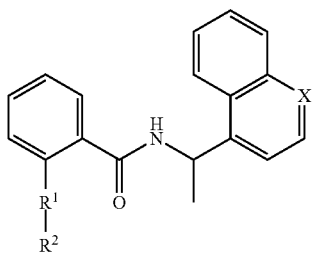

(1d)

wherein $R^1$, $R^2$, and X are as defined under Formula (1), including all of the possible embodiments and combinations thereof described above under Formula (1).

In other specific embodiments of Formula (1), the compound has the following structure:

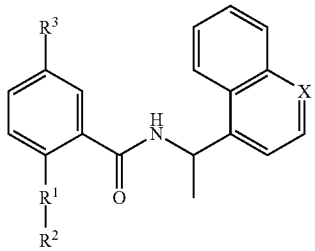

(1e)

wherein $R^1$ and $R^2$ are as defined under Formula (1), including all of the possible embodiments and combinations thereof described above under Formula (1).

In some embodiments, $R^1$ in any of Formulas (1), (1a), (1b), (1c), (1d), and (1e) contains a hydrazide linkage. In some embodiments, $R^2$ in any of Formulas (1), (1a), (1b), (1c), (1d), and (1e) is a group having the formula —C(Y)-E, wherein Y is O or S, and E is a hydrocarbon group containing 1-12 carbon atoms and at least one carbon-carbon or carbon-nitrogen unsaturated bond, such as any such groups described earlier above. In more particular embodiments, $R^2$ in any of Formulas (1), (1a), (1b), (1c), (1d), and (1e) is a group having the formula —C(Y)—(C=C)—C(O)O—V, wherein Y is O or S, and V is a hydrocarbon group containing 1-12 carbon atoms, optionally substituted with one or more F atoms, such as any such groups described earlier above. In further embodiments of any of the foregoing embodiments in which $R^2$ in any of Formulas (1), (1a), (1b), (1c), (1d), and (1e) is a group having the formula —C(Y)—(C=C)—C(O)O—V, V is a bulky hydrocarbon group selected from the group consisting of branched alkyl, alkenyl, and alkynyl groups containing 3-6 carbon atoms; and groups of the formula —(CH$_2$)$_r$—U, wherein U is a carbocyclic or heterocyclic group and r is an integer of 0-3. In other particular embodiments, $R^2$ in any of Formulas (1), (1a), (1b), (1c), (1d), and (1e) is a group having the formula —C(Y)-E, wherein Y is O or S, and E is a hydrocarbon group containing 1-12 carbon atoms and at least one alkyl halide group, such as any such groups described earlier above. In further embodiments of any of the foregoing embodiments in which $R^2$ in any of Formulas (1), (1a), (1b), (1c), (1d), and (1e) is a group having the formula —C(Y)-E, wherein Y is O or S, and E is a hydrocarbon group containing 1-12 carbon atoms and at least one alkyl halide group, $R^2$ has the formula —C(Y)—(CH$_2$)$_s$—W, wherein W is a halogen atom (e.g., F, Cl, Br, or I, more typically Cl).

Any of the compounds described herein according to Formula (1) and sub-formulas thereof may be enantiomerically enriched, enantiomerically pure, or racemic mixture (racemate). For the sake of simplicity, the compounds of the present invention have been depicted without an indication of chirality. However, Formula (1) and sub-formulas thereof are intended to include all possible enantiomers and racemic mixtures. For example, compounds of Formula (1) include the following two enantiomers:

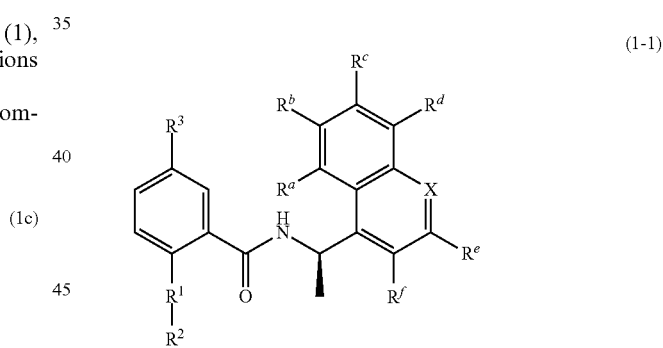

(1-1)

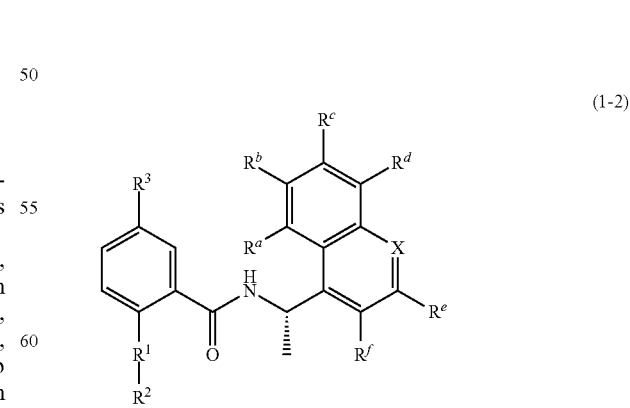

(1-2)

Enantiomerically enriched, enantiomerically pure, and racemic mixture (racemate) forms of any of the above enantiomers of Formula (1) are considered herein.

Similarly, compounds of Formula (1a) include the following two enantiomers:

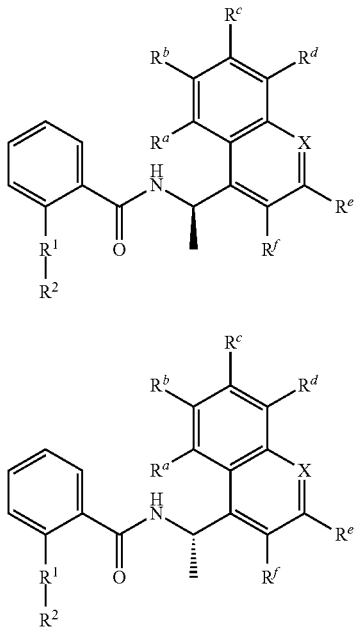

(1a-1)

(1a-2)

Enantiomerically enriched, enantiomerically pure, and racemic mixture (racemate) forms of any of the above enantiomers of Formula (1a) are considered herein.

Similarly, compounds of Formula (1b) include the following two enantiomers:

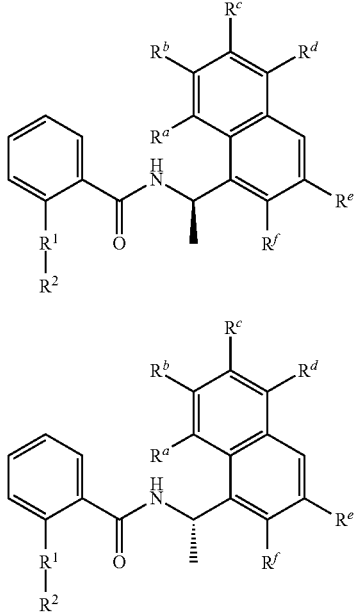

(1b-1)

(1b-2)

Enantiomerically enriched, enantiomerically pure, and racemic mixture (racemate) forms of any of the above enantiomers of Formula (1b) are considered herein.

Similarly, compounds of Formula (1c) include the following two enantiomers:

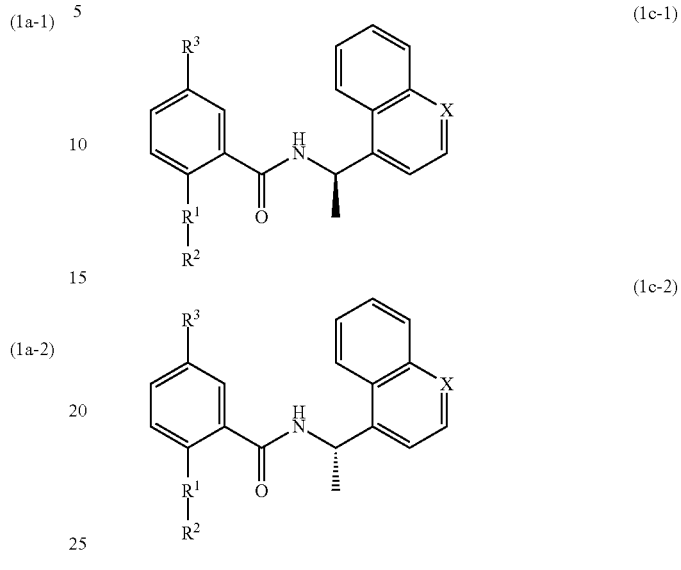

(1c-1)

(1c-2)

Enantiomerically enriched, enantiomerically pure, and racemic mixture (racemate) forms of any of the above enantiomers of Formula (1c) are considered herein.

Similarly, compounds of Formula (1d) include the following two enantiomers:

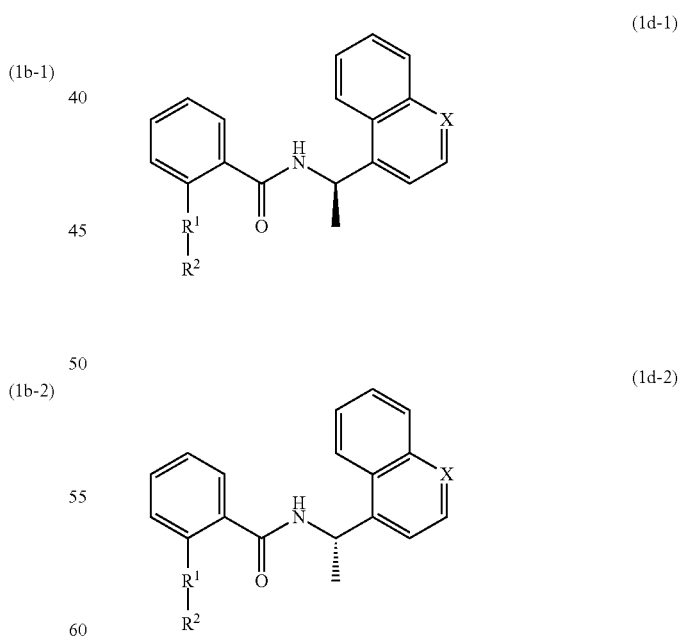

(1d-1)

(1d-2)

Enantiomerically enriched, enantiomerically pure, and racemic mixture (racemate) forms of any of the above enantiomers of Formula (1d) are considered herein.

Similarly, compounds of Formula (1e) include the following two enantiomers:
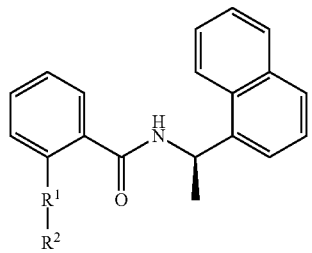
(1e-1)
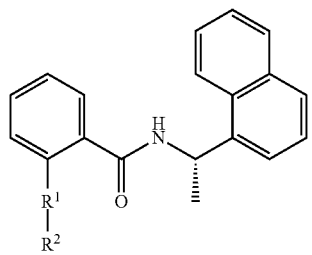
(1e-2)
Enantiomerically enriched, enantiomerically pure, and racemic mixture (racemate) forms of any of the above enantiomers of Formula (1e) are considered herein.
Some specific exemplary compounds within the scope of Formula (1) include the following:
TABLE 1
| Compound No. | Structure |
|---|---|
| 7 | |
| 8 | 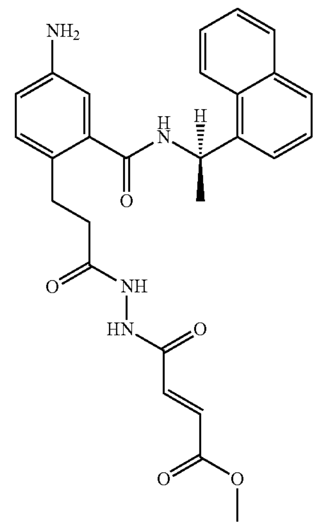 |
| 9 | 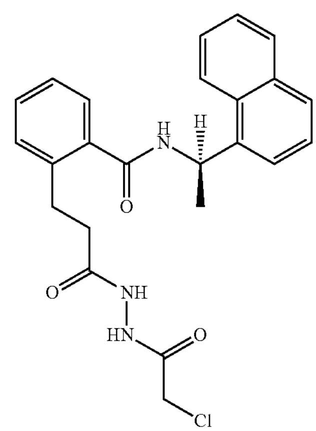 |
| 10 | 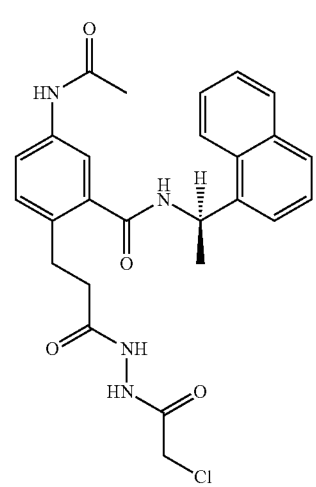 |

TABLE 1-continued
| Compound No. | Structure |
|---|---|
| 11 | 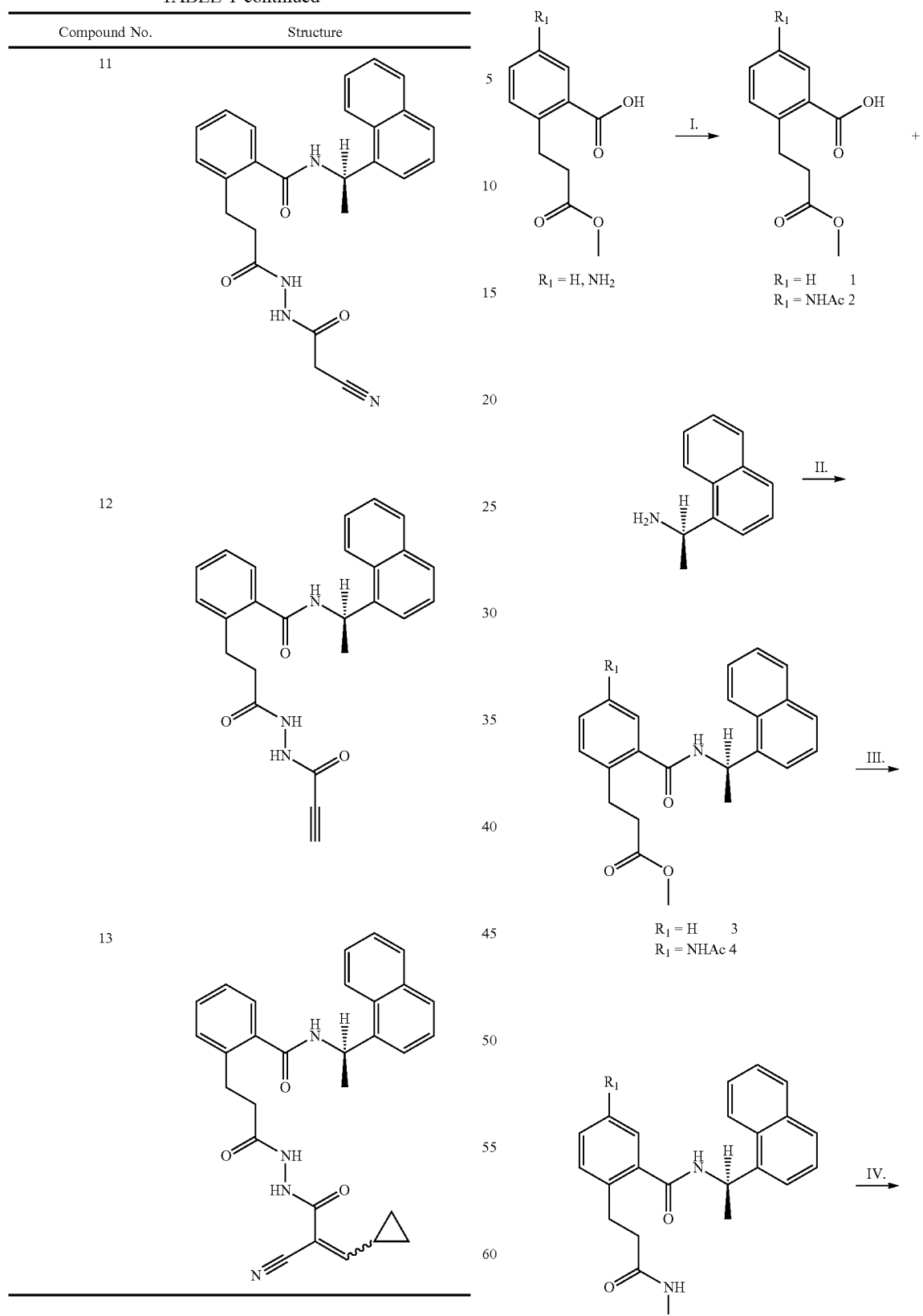 |
| 12 | 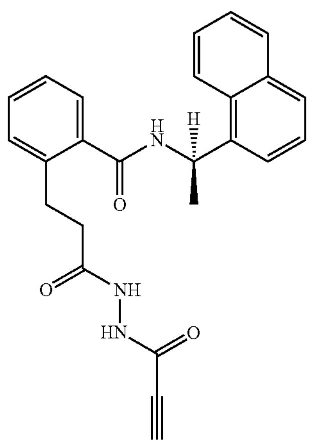 |
| 13 | 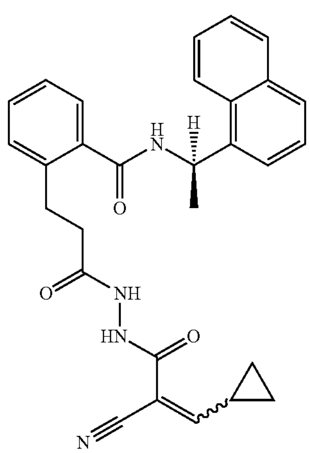 |
The compounds of Formula (1) and sub-formulas thereof can be synthesized by methods well known in the art. A possible synthetic methodology is shown in the following scheme, which is further described in the Examples:

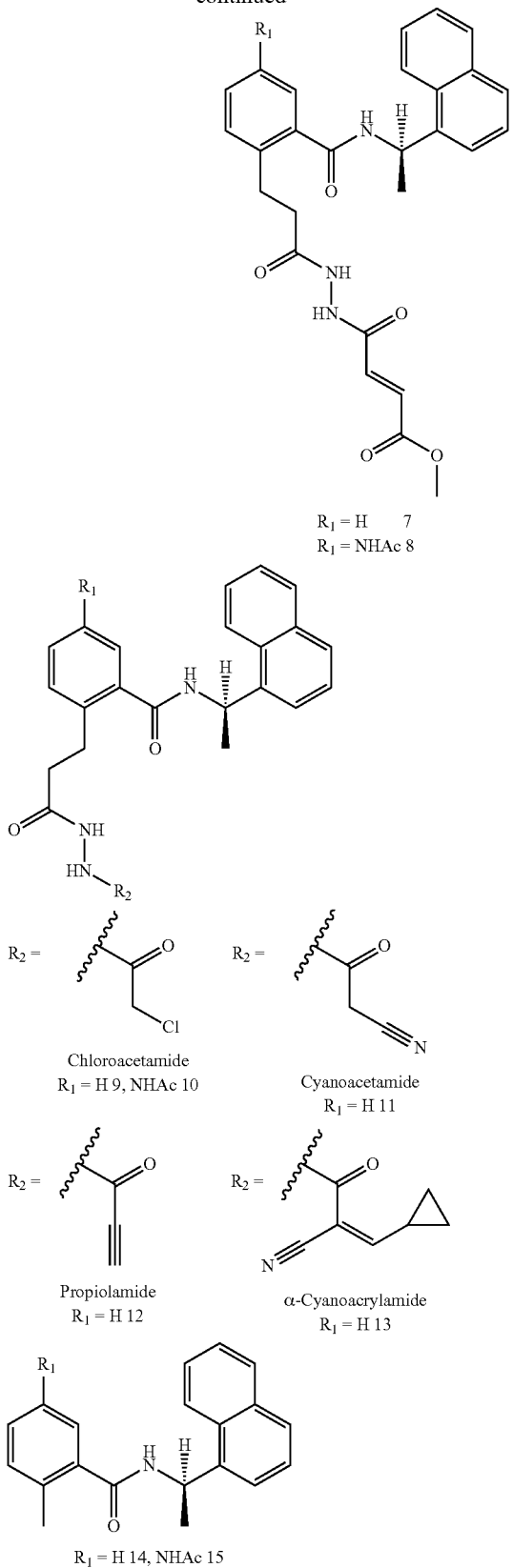

(1e) together with one or more antimicrobial compounds, particularly antiviral compounds, and particularly those active against SARS-CoV-2. The antiviral compound having activity against SARS-CoV-2 typically targets SARS-CoV-2 proteins, such as the viral RNA-dependent RNA polymerase, or the 3CL protease. Some examples of such antivirals include, but are not limited to, remdesivir, molnupiravir, and nirmatrelvir.

Any of the compounds of Formulas (1), (1a), (1b), (1c), (1d), and (1e) can function as coronavirus PLpro inhibitors, and are thus useful in treating or preventing a disease, disorder, or condition mediated by a coronavirus papain-like protease in its roles of generating the viral replicase complex and/or cleaving regulators of host immune pathways such as ubiquitin and ISG15. In particular embodiments, molecules of Formula (1), (1a), (1b), (1c), (1d), or (1e) are useful in inhibiting PLpro activity, viral replicase complex formation, viral replication, and/or cleavage of host immune pathway regulators by coronaviruses such as SARS-CoV, SARS-CoV-2, and related viruses. The molecules of the present invention are also useful in the preparation and execution of screening assays for antiviral compounds. For example, the molecules are useful for identifying PLpro enzyme mutants that are resistant to these molecules, such that they can be used as screening tools for more potent antiviral compounds. The molecules can also be used to establish or determine the binding site of other antivirals to PLpro protease by, for example, competitive inhibition.

Any of the compounds according to Formula (1), (1a), (1b), (1c), (1d), or (1e) may be in the form of a pharmaceutically acceptable salt. As used herein, the term "pharmaceutically acceptable salt" includes both acid and base addition salts, wherein the compound is modified by making acid or base salts thereof. As the compounds described herein typically include at least one amino group or linker (e.g., —NH—), acid addition salts are particularly considered. Examples of pharmaceutically acceptable salts include but are not limited to mineral or organic acid salts of basic residues such as amines.

Pharmaceutically acceptable salts include conventional non-toxic salts or quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids, such as acetic, propionic, succinic, glycolic, stearic, lactic, maleic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, naphthalenesulfonic, methanesulfonic, ethane disulfonic, and oxalic acids. The pharmaceutically acceptable salts of a compound disclosed herein can be synthesized from the parent compound, which contains a basic or acidic moiety, by conventional chemical methods. Suitable salts include those described in P. Heinrich Stahl, Camille G. Wermuth (Eds.), Handbook of Pharmaceutical Salts Properties, Selection, and Use, 2002.

In another aspect, the invention is directed to pharmaceutical compositions that contain any of the above-described compounds of Formulas (1), (1a), (1b), (1c), (1d), or (1e) dispersed in a pharmaceutically acceptable carrier, i.e., vehicle or excipient. The compound is dispersed in the pharmaceutically acceptable carrier by either being mixed (e.g., in solid form with a solid carrier) or dissolved or emulsified in a liquid carrier. The pharmaceutical composition may or may not also be formulated together with one or The present invention also relates to the combination of a molecule of any of Formulas (1), (1a), (1b), (1c), (1d), and more additional active ingredients or adjuvants that improve the overall efficacy of the pharmaceutical composition, particularly as relates to the treatment of infection by a microbe, which may be a bacterium or virus.

The compound and carrier may be formulated into pharmaceutical compositions and dosage forms according to methods well known in the art. The pharmaceutical compositions of the present invention may be specially formulated for administration in liquid or solid form. In some embodiments, the pharmaceutical formulation is formulated for oral administration (e.g., as tablets, capsules, powders, granules, pastes, solutions, suspensions, drenches, or syrups); parenteral administration (e.g., by subcutaneous, intramuscular or intravenous injection as provided by, for example, a sterile solution or suspension); topical application (e.g., as a cream, ointment, or spray); intravaginal or intrarectal administration (e.g., as a pessary, cream or foam); sublingual or buccal administration; ocular administration; transdermal administration; or nasal administration. In some embodiments, the pharmaceutical composition is a liquid formulation designed for administration by injection.

The molecule can be incorporated in a pharmaceutical composition suitable for use as a medicament, for human or animal use. The pharmaceutical compositions may be, for instance, in an injectable formulation, a liquid, cream or lotion for topical application, an aerosol, a powder, granules, tablets, suppositories or capsules, such as for instance, enteric coated capsules, or the like. The pharmaceutical compositions may also be delivered in or on a lipid formulation, such as, for instance, an emulsion or a liposome preparation. The pharmaceutical compositions are preferably sterile, non-pyrogenic and isotonic preparations, optionally with one or more of the pharmaceutically acceptable additives listed below. Pharmaceutical compositions of the molecule are preferably stable compositions which may comprise one or more of the following: a stabilizer, a surfactant, preferably a nonionic surfactant, and optionally a salt and/or a buffering agent. The pharmaceutical composition may be in the form of an aqueous solution, or in a lyophilized form. The stabilizer may, for example, be an amino acid, such as for instance, glycine; or an oligosaccharide, such as for example, sucrose, tetralose, lactose, or a dextran. Alternatively, the stabilizer may be a sugar alcohol, such as for instance, mannitol; or a combination thereof. Preferably, the stabilizer or combination of stabilizers constitutes from about 0.1% to about 10% weight for weight of the molecule. The surfactant is preferably a nonionic surfactant, such as a polysorbate. Some examples of suitable surfactants include Tween20, Tween80; a polyethylene glycol or a polyoxyethylene polyoxypropylene glycol, such as Pluronic F-68 at from about 0.001% (w/v) to about 10% (w/v). The salt or buffering agent may be any salt or buffering agent, such as for example, sodium chloride, or sodium/potassium phosphate, respectively. Preferably, the buffering agent maintains the pH of the pharmaceutical composition in the range of about 5.5 to about 7.5. The salt and/or buffering agent is also useful to maintain the osmolality at a level suitable for administration to a human or an animal. Preferably, the salt or buffering agent is present at a roughly isotonic concentration of about 150 mM to about 300 mM.

The pharmaceutical composition comprising the molecule may additionally contain one or more conventional additive. Some examples of such additives include a solubilizer such as for example, glycerol; an antioxidant such as for example, benzalkonium chloride (a mixture of quaternary ammonium compounds, known as "quats"), benzyl alcohol, chloretone or chlorobutanol; anesthetic agent such as for example a morphine derivative; or an isotonic agent, such as described above. As a further precaution against oxidation or other spoilage, the pharmaceutical compositions may be stored under nitrogen or argon gas in vials sealed with impermeable stoppers.

The phrase "pharmaceutically acceptable" refers herein to those compounds, materials, compositions (e.g., acids or bases), and/or dosage forms which are, within the scope of sound medical judgment, suitable for administration to a subject. The phrase "pharmaceutically acceptable carrier," as used herein, refers to a pharmaceutically acceptable vehicle, such as a liquid or solid filler, diluent, carrier, manufacturing aid (e.g., lubricant, talc magnesium, calcium or zinc stearate, or stearic acid), solvent, or encapsulating material, that serves to carry the therapeutic composition for administration to the subject. Each carrier should be "acceptable" in the sense of being compatible with the other ingredients of the formulation and physiologically safe to the subject. Any of the carriers known in the art can be suitable herein depending on the mode of administration.

Some examples of materials that can serve as pharmaceutically-acceptable carriers include water; isotonic saline; pH buffering agents; and sugars (e.g., lactose, glucose, sucrose, and oligosaccharides, such as sucrose, trehalose, lactose, or dextran). Other excipients, more typically used in solid dosage forms, may also be included, e.g., starches (e.g., corn and potato starch); cellulose and its derivatives (e.g., sodium carboxymethyl cellulose, ethyl cellulose and cellulose acetate); gelatin; talc; waxes; oils (e.g., peanut oil, cottonseed oil, safflower oil, sesame oil, olive oil, corn oil and soybean oil); glycols (e.g., ethylene glycol, propylene glycol, and polyethylene glycol); polyols (e.g., glycerin, sorbitol, and mannitol); esters (e.g., ethyl oleate and ethyl laurate); agar; and other non-toxic compatible substances employed in pharmaceutical formulations. If desired, certain sweetening and/or flavoring and/or coloring agents may be added. Other suitable excipients can be found in standard pharmaceutical texts, e.g., in "Remington's Pharmaceutical Sciences", The Science and Practice of Pharmacy, 19th Ed. Mack Publishing Company, Easton, Pa., (1995).

In another aspect, the present disclosure is directed to methods of inhibiting papain-like protease (PLpro) activity in a subject by administering to the subject a therapeutically effective dosage of a compound of Formula (1) to result in inhibition of PLpro activity in the subject. In particular embodiments, the PLpro activity is mediated by a coronavirus PLpro. In some embodiments, the method is more particularly a method of treating coronavirus infection in a subject by administering a therapeutically effective dosage of a compound of Formula (1) to the subject to result in inhibition or prevention of one or more coronavirus symptoms in the subject. The subject being treated may be confirmed to have been infected with coronavirus or may display symptoms consistent with coronavirus infection or may at risk for infection with coronavirus.

In another aspect, the covalent inhibitor molecules having the general structural Formula (1) described herein are useful in inhibiting papain-like protease activity, viral replicase complex formation, viral replication, and/or host immune pathway regulator cleavage of coronaviruses such as SARS-CoV, SARS-CoV-2, and related viruses. The method includes contacting the papain-like protease with a covalent inhibitor molecule having the generic structural Formula (1) or sub-generic formula described herein.

In further aspects, the invention provides a method for treating or preventing a disease, disorder, or condition mediated by a coronavirus papain-like protease in a mammal in need thereof. The method includes administering to the mammal a covalent inhibitor molecule having the generic structural Formula (1) or sub-generic formula described herein. The mammal is typically a human, but may be a farm animal, such as a goat, horse, pig, or cow; a pet animal, such as a dog or cat; a laboratory animal, such as a mouse, rat, or guinea pig; or a primate, such as a monkey, orangutan, ape, chimpanzee, or human.

The molecules of Formula (1) inhibit SARS-CoV-2 papain-like protease and thereby have a range of applications, such as therapeutic application, because of the role that the papain-like protease (PLpro) plays in the physiology of SARS-CoV-2 replication and host infection. The reaction catalyzed by PLpro is the proteolytic cleavage of two viral polyproteins, pp1a and pp1ab, to produce the proteins Nsp1, Nsp2 and Nsp3. The first identified coronavirus PLpro was identified in the genome of a murine coronavirus (S. C. Baker et al., *J. Virol.*, 63, 3693-3699 (1989). PLpro was later established as a therapeutic target (K. Ratia et al., *Proc Natl Acad Sci USA* 105, 16119-16124 (2008). A respiratory disease treatable with PLpro inhibitors within the scope of Formula (1) is coronavirus disease 2019 (COVID-19).

An effective amount of the molecule, preferably in a pharmaceutical composition, may be administered to a human or an animal in need thereof by any of a number of well-known methods. For example, the molecule may be administered systemically or locally, such as by injection. The systemic administration of the molecule may be by intravenous, subcutaneous, intraperitoneal, intramuscular, intrathecal, or oral administration. An effective amount of a pharmaceutical composition of the invention is any amount that is effective to achieve its purpose. The effective amount, usually expressed in mg/kg can be determined by routine methods during pre-clinical and clinical trials by those of skill in the art. Dosing is dependent on the severity and responsiveness of the infection being treated, with the course of treatment lasting from several days to several months, or until a cure is effected or a diminution of the disease state is achieved. Optimal dosing schedules can be calculated from measurements of drug accumulation in the body of the patient. The administering physician can determine optimum dosages, dosing methodologies, and repetition rates. In different embodiments, depending on these and other factors, a suitable dosage of the active ingredient may be precisely, at least, or no more than, for example, 1 mg, 10 mg, 50 mg, 100 mg, 200 mg, 300 mg, 400 mg, 500 mg, 600 mg, 700 mg, 800 mg, 900 mg, 1000 mg, 1200 mg, or 1500 mg, per 50 kg, 60 kg, or 70 kg adult, or a dosage within a range bounded by any of the foregoing exemplary dosages. Depending on these and other factors, the composition is administered in the indicated dosage by any suitable schedule, e.g., once, twice, or three times a day for a total treatment time of one, two, three, four, or five days, and up to, for example, one, two, three, or four weeks or months. The indicated dosage may alternatively be administered every two or three days, or per week. Alternatively, or in addition, the composition is administered until a desired change is evidenced.

In yet another aspect, a molecule having the generic structural Formula (1) described herein is also useful in the preparation and execution of screening assays for antiviral compounds. For example, the molecules are useful for identifying PLpro enzyme mutants that are resistant to these molecules, such that they can be used as screening tools for more potent antiviral compounds. The molecules can also be used to establish or determine the binding site of other antivirals to PLpro protease, for example by competitive inhibition.

The ability of the molecule of Formula (1) to inhibit PLpro may be demonstrated using a SARS-COV-2 PLpro enzyme inhibition assay using a fluorogenic peptide. For example, a recombinantly produced and purified SARS-COV-2 PLpro activity is assayed in the presence and absence of a molecule of Formula (1) at varying concentrations and preincubation times, with Z-RLRGG-AMC or LRGG-AMC as substrate. These assays provide a means to compare the activities of molecules of Formula (1) to their prodrugs, salts, and formulations, and can be varied by those skilled in the art.

Inhibitors may be characterized by dispensing enzyme solution into wells, followed by inhibitor solution, and incubation for 30 min. Reactions may be initiated by adding substrate and initial rates are then determined. $IC_{50}$ values at a single fixed time point (e.g., after 30-minute preincubation) may be determined by non-linear regression to the [Inhibitor] vs. normalized response. This assay can be used to measure $IC_{50}$ and adapted to obtain time dependent $IC_{50}$ values and thereby identify structure activity relationships. It can also be used as a high-throughput screen to identify new compounds with PLpro protease inhibition activity.

Time-dependent PLpro inhibition assays can be performed as described above, except that preincubation times are varied by adding the inhibitor to the enzyme at multiple specific time points. For each inhibitor concentration, initial rates are normalized and plotted against preincubation time. Non-linear regression is then performed to determine rate constants $k_{obs}$ for each concentration. These rate constants are then plotted against inhibitor concentration, and the data in the initial linear region can be fit to determine the slope, which is kinact/KI. Another such assay assesses the inhibition of PLpro-catalyzed cleavage of ubiquitin and/or ISG15 using ubiquitin-rhodamine or ISG15-CHOP2 as substrates. The CHOP2 reporter is inactive when linked to ISG15 but becomes catalytically active upon cleavage by PLpro. Thus, this coupled assay produces a signal upon cleavage of CHOP2 that quantitatively measures the activity of PLpro.

Another such assay can be performed using, for instance, Vero E6 cells to measure the cytopathic effect (CPE) protection for the 50% efficacy concentration ($EC_{50}$) and cytotoxicity ($CC_{50}$). Compounds can be evaluated at several concentrations using a luminescent cell viability assay to obtain $EC_{50}$ and $CC_{50}$ values. Briefly, Vero E6 TMPRSS ACE2 cells are grown, for example, to ~90% confluency and treated for an amount of time, such as, for example, 1 hr, with compounds. Cells are then infected at an appropriate MOI (e.g., ~0.1) with a viral isolate such as SARS-CoV-2 strain USA-WA1/2020. After some given time, for example, 48 h, the virally mediated CPE and cytotoxicity are assessed by measurement of live cells using the luminescent cell viability assay.

Examples have been set forth below for the purpose of illustration and to describe certain specific embodiments of the invention. However, the scope of this invention is not to be in any way limited by the examples set forth herein.

Examples

Overview

In describing the examples, chemical elements are identified in accordance with the Periodic Table of the Elements. Abbreviations and symbols used herein are in accordance with the common usage of such abbreviations and symbols by those skilled in the chemical arts. The following abbreviations are used herein:

aq aqueous
AMC aminomethylcoumarin
CPE cytopathic effect
DMSO dimethylsulfoxide
CC50 50% cytotoxic concentration
EC50 50% effective concentration
IC50 50% inhibition concentration
MOI multiplicity of infection
SARS Severe Acute Respiratory Syndrome
SI50 selectivity index at 50%

Unless otherwise noted, all starting materials were obtained from commercial suppliers and used without further purification. Unless otherwise indicated, all temperatures are expressed in ° C. (degrees Celsius). Unless otherwise indicated, all reactions were conducted under an inert atmosphere at ambient temperature.

All temperatures are given in degrees Celsius. All solvents are of the highest available purity and all reactions were run under anhydrous conditions in an argon (Ar) or nitrogen ($N_2$) atmosphere where necessary.

The following examples illustrate the invention. These examples are not intended to limit the scope of the present invention, but rather to provide guidance to the skilled artisan to prepare and use the compounds, compositions, and methods of the present invention.

Synthesis of Compounds of Formula (1)

Selected compounds of Formula (1) were synthesized in accordance with the following synthetic scheme:

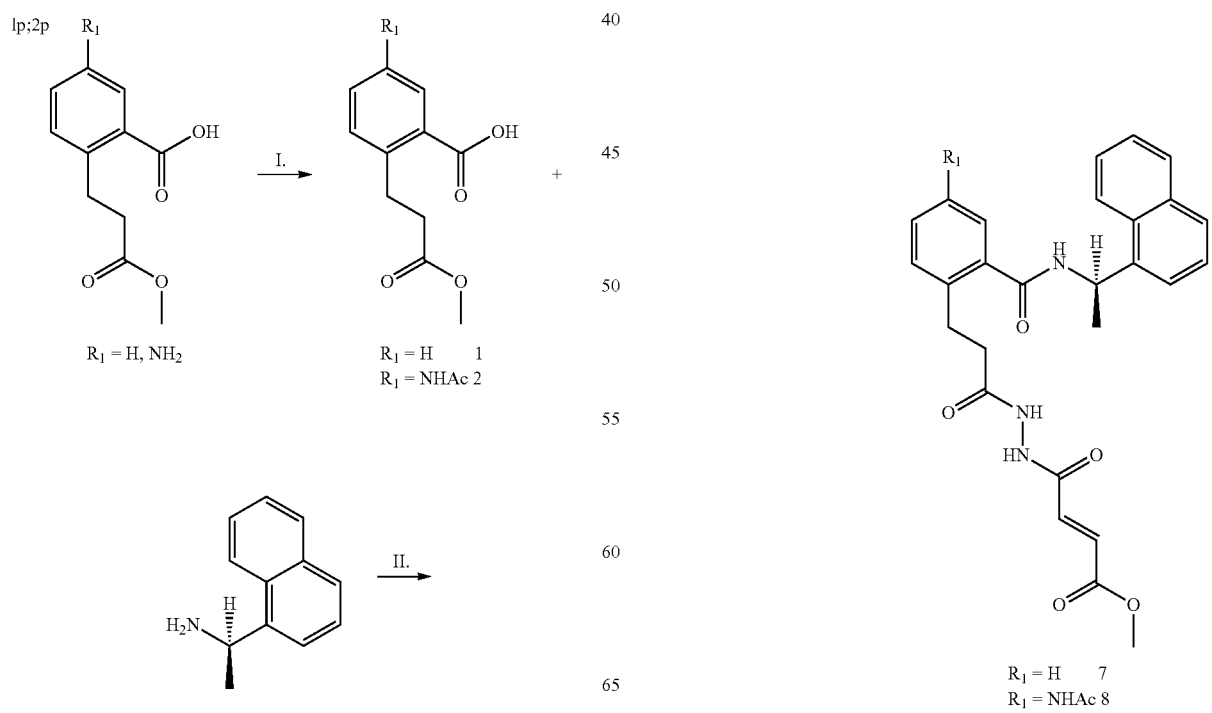

-continued

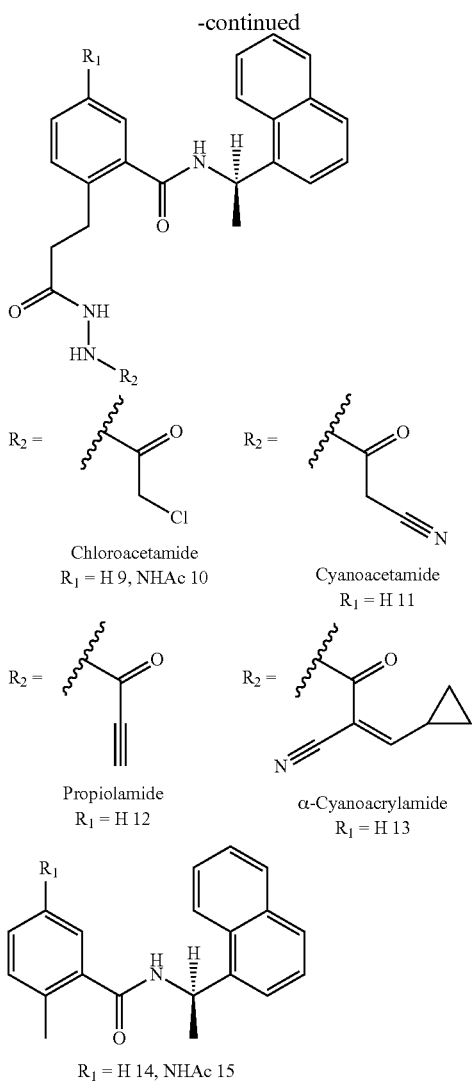

The above scheme shows the synthesis of compounds 2-15. Reaction conditions with yields in parentheses: I. Ac₂O, AcOH, DCM, 55%; II. HATU, DIPEA, DCM (3, 83%; 4, 91%); III. N₂H₄·H₂O, EtOH (5 and 6, 97%); IV. methyl (E)-4-chloro-4-oxobut-2-enoate, DIPEA, DCM for 7 (56%), and K₂CO₃, DMF for 8 (34%). Compounds 9 (50%), 10 (37%), 11 (56%), 12 (23%), and 13 (60%) were prepared with the corresponding acid chlorides under conditions described for step IV. Compounds 14 (89%) and 15 (83%) were prepared analogously to step II with 2-methylbenzoic acid and 5-acetamido-2-methylbenzoic acid, respectively.

Synthesis and Characterization of Compounds. All reagents were purchased from commercial suppliers and used as received unless otherwise noted. Anhydrous acetonitrile (MeCN), dichloromethane (CH₂Cl₂), ethanol (EtOH), dimethylformamide (DMF), tetrahydrofuran (THF), methanol (MeOH), and diethyl ether (Et₂O) were purchased from commercial sources and maintained under dry N₂ conditions. Amide couplings and reactions with acid chlorides were performed under N₂ using standard Schlenk-line techniques. Compound 1 was purchased from commercial sources and used as received. ¹H and ¹³C NMR spectra were recorded in the listed deuterated solvent with a 500 MHz NMR spectrometer at 298 K with chemical shifts referenced to the residual protio signal of the deuterated solvent as previously reported (G. R. Fulmer et al., Organometallics, 29(9), 2176-2179, 2010). Low-resolution mass data were collected on an Agilent 6470AA Triple Quadrupole LC/MS system. High-resolution mass data were collected on a Waters Synapt HDMS QTOF mass spectrometer. Following the initial synthesis and screening of compounds 2-15, compound 7 was produced on the gram-scale following the same procedures described below. Purity was analyzed by analytical HPLC and Thermo LTQ MS with electrospray ionization in the positive mode with a Waters BEH 130, 5 μm, 4.6×150 mm C18 column, linear gradient from 90:10 to 0:100 water/acetonitrile in 10 min at a flow rate of 1 mL/min.

5-acetamido-2-(3-methoxy-3-oxopropyl)benzoic acid (2). To a 15 mL solution of DCM was added 0.300 g (1.344 mmol) of 5-amino-2-(3-methoxy-3-oxopropyl)benzoic acid and cooled to 0° C. Acetic anhydride (1.3 mL, ~13 mmol) was added slowly while stirring. The solution was allowed to reach RT overnight, followed by addition of saturated NH₄Cl and extraction with DCM (3×50 mL). The organic phases were combined and dried with MgSO₄ and concentrated under reduced pressure to afford a pale-yellow syrup (0.195 g, 0.735 mmol, 55%). ¹H NMR (500 MHz, DMSO-d₆, δ from residual protio solvent) δ 12.40 (s, br, 1H), 10.00 (s, 1H), 8.03 (s, 1H), 7.67 (d, J=8.3 Hz, 1H), 7.23 (d, J=8.3 Hz, 1H), 3.57 (s, 3H), 3.10 (t, J=7.7 Hz, 2H), 2.56 (t, J=7.7 Hz, 2H), 2.03 (s, 3H). ¹³C NMR (126 MHz, DMSO, δ from solvent) δ 172.61, 168.32, 137.54, 135.83, 131.09, 130.43, 122.18, 120.75, 51.18, 35.08, 28.50, 23.88, 20.99. LRMS-ESI (m/z): [M+H]⁺ Theoretical for C₁₃H₁₅NO₅: 266.1; Experimental: 266.1.

methyl (R)-3-(2-((1-(naphthalen-1-yl)ethyl)carbamoyl) phenyl)-propanoate (3). A 20 mL DCM solution containing 2-(3-methoxy-3-oxopropyl)benzoic acid (0.500 g, 2.4 mmol) was cooled to 0° C. followed by addition of HBTU (1.138 g, 3.0 mmol). This solution was stirred for 30 min, followed by addition of (R)-1-(naphthalen-1-yl)ethan-1-amine (0.409 g, 2.4 mmol) and DIPEA (0.522 mL, 3.0 mmol). The solution was warmed to RT and stirred for 16 h. The reaction mixture was quenched with 50 mL of H₂O and extracted with DCM (3×50 mL). The organic layers were collected and dried with MgSO₄ and concentrated under reduced pressure. The residue was purified by silica gel chromatography using 3:1 Hexanes:EtOAc (R$_f$=0.36) to afford a white solid. Washes were performed, and the resulting solid was dried under reduced pressure. This workup afforded the product as an off-white solid (0.723 g, 2.0 mmol, 83%). ¹H NMR (500 MHz, DMSO-d₆) δ from residual protio solvent 8.95 (d, J=7.9 Hz, 1H), 8.24 (d, J=8.4 Hz, 1H), 7.95 (d, J=8.0 Hz, 1H), 7.84 (d, J=8.1 Hz, 1H), 7.65-7.46 (m, 4H), 7.38-7.29 (m, 2H), 7.30-7.23 (m, 2H), 5.92 (p, J=7.2 Hz, 1H), 3.57 (s, 3H), 2.92 (t, J=8.0 Hz, 2H), 2.57 (t, J=7.9 Hz, 2H), 1.58 (d, J=6.9 Hz, 3H). ¹³C NMR (126 MHz, DMSO, δ from solvent): 172.51, 168.02, 140.12, 138.11, 136.96, 133.36, 130.39, 129.56, 129.34, 128.62, 127.29, 127.19, 126.11, 126.00, 125.56, 125.43, 123.11, 122.46, 51.21, 44.36, 34.96, 27.96, 21.36. HRMS-ESI (m/z): [M+H]⁺ Theoretical for C₂₃H₂₄NO₃: 362.1756; Experimental: 362.1745.

methyl (R)-3-(4-acetamido-2-((1-(naphthalen-1-yl)ethyl) carbamoyl)-phenyl)propanoate (4). Compound 4 was prepared similarly to the amide coupling of 3. The amount of materials used were: 2 (0.350 g, 1.08 mmol); HBTU (0.899 g, 2.15 mmol); (R)-1-(naphthalen-1-yl)ethan-1-amine (0.366 g, 2.15 mmol) and DIPEA (0.749 mL, 4.30 mmol). Silica gel column purification was performed under a gradient from 1:1, 2:1, 3:1 EtOAc:Hexanes at 1 column volume for each gradient step. Compound 4 was isolated as white solid (0.410 g, 0.980 mmol, 91%). $^1$H NMR (500 MHz, DMSO-$d_6$, δ from residual protio solvent) δ 9.96 (s, 1H), 8.95 (d, J=8.0 Hz, 1H), 8.24 (d, J=8.4 Hz, 1H), 7.95 (dd, J=8.0, 1.6 Hz, 1H), 7.84 (d, J=8.2 Hz, 1H), 7.64-7.55 (m, 3H), 7.54 (ddd, J=8.1, 6.8, 1.3 Hz, 1H), 7.52-7.45 (m, 2H), 7.17 (d, J=8.4 Hz, 1H), 5.92 (p, J=7.2 Hz, 1H), 3.56 (s, 3H), 2.83 (t, J=7.8 Hz, 2H), 2.69 (s, 3H), 2.53 (t, J=8.0 Hz, 2H), 2.02 (s, 3H), 1.57 (d, J=6.9 Hz, 3H). $^{13}$C NMR (126 MHz, DMSO, δ from solvent) δ 172.50, 168.22, 167.88, 140.07, 137.33, 137.26, 133.33, 132.26, 130.39, 129.78, 128.60, 127.19, 126.14, 125.56, 125.36, 123.08, 122.39, 119.69, 117.71, 51.17, 44.22, 38.19, 35.02, 27.39, 23.85, 21.39. LRMS-ESI (m/z): [M+H]$^+$ Theoretical for $C_{25}H_{26}N_2O_4$: 419.2; Experimental: 419.2.

(R)-2-(3-hydrazineyl-3-oxopropyl)-N-(1-(naphthalen-1-yl)ethyl)benzamide (5). To a 10 mL EtOH solution containing 1 (0.400 g, 1.11 mmol) was added 0.5 mL (~1 M) of hydrazine monohydrate ($N_2H_4$ 64-65%, reagent grade 95%). The pale-yellow, homogenous solution was refluxed for 16 h. The resulting solution was reduced under vacuum to afford an off-white powder. To remove excess hydrazine monohydrate, several (3×15 mL) $Et_2O$ washes were performed, and the resulting solid was dried under reduced pressure. This workup afforded the product as an off-white solid (0.390 g, 1.08 mmol, 97%). $^1$H NMR (500 MHz, DMSO-$d_6$, δ from residual protio solvent): 8.97 (d, J=7.9 Hz, 1H), 8.91 (s, 1H), 8.25 (d, J=8.5 Hz, 1H), 7.96 (d, J=8.1 Hz, 1H), 7.84 (d, J=8.1 Hz, 1H), 7.65 (d, J=7.2 Hz, 1H), 7.61 (t, J=7.6 Hz, 1H), 7.54 (dt, J=15.0, 7.6 Hz, 2H), 7.35 (t, J=7.4 Hz, 1H), 7.31 (d, J=7.4 Hz, 1H), 7.28-7.21 (br, 2H), 5.93 (p, J=7.2 Hz, 1H), 4.21 (s, 2H), 2.91 (td, J=7.5, 4.3 Hz, 2H), 2.35 (t, J=7.9 Hz, 2H), 1.60 (d, J=6.9 Hz, 3H). $^{13}$C NMR (126 MHz, DMSO, δ from solvent): 170.82, 168.04, 140.20, 138.74, 137.05, 133.35, 130.37, 129.22, 129.20, 128.61, 127.21, 127.16, 126.14, 125.72, 125.55, 125.50, 123.12, 122.46, 44.42, 34.85, 28.22, 21.44. HRMS-ESI (m/z): [M+H]$^+$ Theoretical for $C_{22}H_{24}N_3O_2$: 362.1859; Experimental: 362.1885.

(R)-5-acetamido-2-(3-hydrazineyl-3-oxopropyl)-N-(1-(naphthalen-1-yl)ethyl)benzamide (6). Compound 6 was prepared analogously to 5. The amounts of materials used were: 4 (0.400 g, 0.956 mmol); 10 mL EtOH solution containing; 0.5 mL (~1M) of hydrazine monohydrate ($N_2H_4$ 64-65%, reagent grade 95%). This procedure afforded an off-white solid (0.388 g, 0.927 mmol, 97%) ($^1$H NMR (500 MHz, DMSO-$d_6$, δ from residual protio solvent) δ 9.94 (s, 1H), 8.97 (d, J=7.9 Hz, 1H), 8.89 (s, 1H), 8.24 (d, J=8.4 Hz, 1H), 7.95 (d, J=8.1 Hz, 1H), 7.84 (d, J=8.0 Hz, 1H), 7.65-7.56 (m, 3H), 7.53 (dt, J=18.1, 7.5 Hz, 2H), 7.45 (s, 1H), 7.15 (d, J=8.4 Hz, 1H), 5.92 (p, J=6.9 Hz, 1H), 4.11 (s, br, 2H), 2.82 (hept, J=7.5, 7.0 Hz, 2H), 2.31 (t, 2H), 2.01 (s, 3H), 1.58 (d, J=7.0 Hz, 3H). $^{13}$C NMR (126 MHz, DMSO, δ from solvent) δ 170.85, 168.18, 167.90, 140.17, 137.40, 137.02, 133.34, 132.89, 130.39, 129.42, 128.60, 127.18, 126.17, 125.57, 125.44, 123.11, 122.39, 119.68, 117.66, 44.31, 34.89, 27.65, 23.85, 21.48. LRMS-ESI (m/z): [M+H]$^+$ Theoretical for $C_{25}H_{26}N_4O_3$: 419.2; Experimental: 419.2.

Preparation of compounds with electrophilic warheads. Compounds 7, 9, 11, and 13 were prepared by taking 0.030 g (0.083 mmol) of 5 and 0.029 mL (0.166 mmol) of DIPEA into 5 mL anhydrous DCM under $N_2$ atmosphere. Once dissolved, 0.100 mmol (1.2 equiv.) of appropriate acid chloride was added while stirring under $N_2$ atmosphere. Rapid reaction resulted in precipitation of a white solid. The reaction was left at RT for 2 h with no observable changes. The DCM was removed under reduced pressure and $Et_2O$ was added to the remaining residue to precipitate a white solid that was collected with a 2 mL fritted glass funnel. The remaining white solid was washed extensively with $Et_2O$, dried, and collected. Isolated yields: 7 (0.022 g, 0.046 mmol, 56%); 9 (0.018 g, 0.041 mmol, 50%); 11 (0.020 g, 0.047 mmol, 56%); 13 (0.024 g, 0.050 mmol, 60%).

Compounds 8 and 10 were prepared by placing 0.040 g (0.096 mmol) of 6 in 5 mL of anhydrous DMF followed by addition of $K_2CO_3$ (0.020 g, 0.145 mmol). The solution was stirred while 0.115 mmol (1.2 equiv.) of appropriate acid chloride was added. The solution was stirred at RT for 2 h followed by addition of 25 mL EtOAc and extraction with 3×25 mL of $H_2O$ to remove DMF. The organic layers were combined, dried with $MgSO_4$, and concentrated under reduced pressure. The crude residue was purified by silica gel flash chromatography using pure EtOAc with 1-5% MeOH to yield white solids: 8 (0.016 g, 0.032 mmol, 34%); 10 (0.019 g, 0.036 mmol, 37%).

methyl(R,E)-4-(2-(3-(2-((1-(naphthalen-1 yl)ethyl)carbamoyl)-phenyl)propanoyl)hydrazineyl)-4-oxobut-2-enoate (7). $^1$H NMR (500 MHz, DMSO-$d_6$, δ from residual protio solvent) δ 10.53 (s, 1H), 10.16 (s, 1H), 8.93 (d, J=7.9 Hz, 1H), 8.24 (d, J=8.6 Hz, 1H), 7.95 (d, J=8.1 Hz, 1H), 7.83 (d, J=8.2 Hz, 1H), 7.67-7.57 (m, 2H), 7.56-7.48 (m, 2H), 7.39-7.21 (m, 4H), 7.08 (d, J=15.6 Hz, 1H), 6.69 (dd, J=15.5, 1.9 Hz, 1H), 5.93 (p, J=7.3 Hz, 1H), 3.75 (s, 3H), 2.94 (dt, J=8.8, 5.0 Hz, 2H), 2.55-2.47 (m, 3H overlaps with DMSO-$d_6$), 1.59 (d, J=6.9 Hz, 3H). $^{13}$C NMR (126 MHz, DMSO, δ from solvent) δ 170.30, 168.56, 165.73, 161.57, 140.66, 139.06, 137.56, 135.58, 133.86, 130.91, 129.90, 129.82, 129.77, 129.13, 127.73, 127.70, 126.67, 126.35, 126.08, 126.02, 123.65, 122.96, 52.59, 44.94, 35.14, 28.56, 21.92. HRMS-ESI (m/z): [M+H]$^+$ Theoretical for $C_{27}H_{28}N_3O_5$: 474.2029; Experimental: 474.2007.

methyl-(R,E)-4-(2-(3-(4-acetamido-2-((1-(naphthalen-1-yl)ethyl)carbamoyl)phenyl)propanoyl)hydrazineyl)-4-oxobut-2-enoate (8). $^1$H NMR (500 MHz, DMSO-$d_6$, δ from residual protio solvent) δ 10.52 (s, 1H), 10.15 (s, 1H), 9.95 (s, 1H), 8.93 (d, J=7.9 Hz, 1H), 8.24 (d, J=8.6 Hz, 1H), 7.95 (d, J=8.0 Hz, 1H), 7.83 (d, J=8.2 Hz, 1H), 7.64-7.57 (m, 3H, 7.56-7.48 (m, 2H), 7.45 (s, 1H), 7.21 (d, J=8.4 Hz, 1H), 7.07 (d, J=15.6 Hz, 1H), 6.68 (d, J=15.5 Hz, 1H), 5.93 (p, J=7.2 Hz, 1H), 3.75 (s, 3H), 2.86 (m, 2H), 2.47 (m, 2H), 2.02 (s, 3H), 1.57 (d, J=6.9 Hz, 3H). $^{13}$C NMR (126 MHz, DMSO, δ from solvent) δ 169.79, 168.17, 167.88, 165.18, 161.03, 140.09, 137.38, 137.09, 135.02, 133.31, 132.65, 130.37, 129.57, 129.22, 128.57, 127.17, 126.16, 125.55, 125.41, 123.09, 122.34, 119.68, 117.60, 52.04, 44.27, 34.64, 27.45, 23.83, 21.41. HRMS-ESI (m/z): [M+H]$^+$ Theoretical for $C_{29}H_{31}N_4O_6$: 531.2244; Experimental: 531.2217.

(R)-2-(3-(2-(2-chloroacetyl)hydrazineyl)-3-oxopropyl)-N-(1-(naphthalen-1-yl)ethyl)benzamide (9). $^1$H NMR (500 MHz, DMSO-$d_6$, δ from residual protio solvent) δ 10.21 (s, 1H), 9.98 (s, 1H), 8.95 (d, J=7.8 Hz, 1H), 8.24 (d, J=8.5 Hz, 1H), 7.96 (d, J=8.1 Hz, 1H), 7.84 (d, J=8.1 Hz, 1H), 7.67-7.49 (m, 4H), 7.38-7.23 (m, 4H), 5.93 (p, J=7.2 Hz, 1H), 4.14 (s, 2H), 2.94 (t, J=9.1, 2H), 2.48 (t, J=9.1 Hz, 2H), 1.60 (d, J=6.8 Hz, 3H). $^{13}$C NMR (126 MHz, DMSO, δ from solvent) δ 170.08, 168.06, 164.65, 140.15, 138.56, 137.04, 133.35, 130.39, 129.39, 129.31, 128.62, 127.20 (two overlapping $^{13}$C signals), 126.16, 125.83, 125.58, 125.51, 123.14, 122.45, 44.43, 40.86, 34.62, 28.02, 21.41 HRMS-ESI (m/z): [M+H]$^+$ Theoretical for $C_{24}H_{25}ClN_3O_3$: 438.1584; Experimental: 438.1565.

(R)-5-acetamido-2-(3-(2-(2-chloroacetyl)hydrazineyl)-3-oxopropyl)-N-(1-(naphthalen-1-yl)ethyl)benzamide (10). $^1$H NMR (500 MHz, DMSO-$d_6$, δ from residual protio solvent) δ 10.20 (s, 1H), 9.96 (s, 2H), 8.94 (d, J=8.0 Hz, 1H), 8.25 (d, J=8.5 Hz, 1H), 7.96 (d, J=8.1 Hz, 1H), 7.85 (d, J=8.2 Hz, 1H), 7.62 (q, J=6.7 Hz, 3H), 7.54 (m, 2H), 7.46 (s, 1H), 7.21 (d, J=8.4 Hz, 1H), 5.93 (q, J=7.3 Hz, 1H), 4.14 (s, 2H), 2.86 (m, 2H), 2.45 (t, J=7.9 Hz, 2H), 2.03 (s, 3H), 1.58 (d, J=6.8 Hz, 3H). $^{13}$C NMR (126 MHz, DMSO, δ from solvent) δ 170.60, 168.72, 168.43, 165.14, 140.64, 137.92, 137.63, 133.86, 133.21, 130.92, 130.12, 129.12, 127.72, 126.71, 126.10, 125.97, 123.64, 122.89, 120.23, 118.13, 44.82, 41.37, 35.18, 27.97, 24.38, 21.96. HRMS-ESI (m/z): [M+H]$^+$ Theoretical for $C_{26}H_{28}ClN_4O_4$: 495.1799; Experimental: 495.1788.

(R)-2-(3-(2-(2-cyanoacetyl)hydrazineyl)-3-oxopropyl)-N-(1-(naphthalen-1-yl)ethyl)benzamide (11). $^1$H NMR (500 MHz, DMSO-$d_6$, δ from residual protio solvent) δ 10.16 (s, 1H), 9.96 (s, 1H), 8.93 (d, J=7.8 Hz, 1H), 8.23 (d, J=8.5 Hz, 1H), 7.95 (d, J=8.2 Hz, 1H), 7.83 (d, J=8.2 Hz, 1H), 7.66-7.57 (m, 2H), 7.57-7.48 (m, 2H), 7.39-7.21 (m, 4H), 5.92 (p, J=7.1 Hz, 1H), 3.74 (s, 2H), 2.97-2.89 (t, 7.6 Hz, 2H), 2.47 (t, J=7.6 Hz, 2H), 1.59 (d, J=6.9 Hz, 3H). $^{13}$C NMR (126 MHz, DMSO, δ from solvent) δ 170.13, 168.03, 161.12, 140.14, 138.52, 137.02, 133.34, 130.39, 129.39, 129.29, 128.61, 127.20, 127.18, 126.15, 125.82, 125.57, 125.50, 123.13, 122.44, 115.62, 44.41, 34.55, 27.99, 23.67, 21.39. HRMS-ESI (m/z): [M+H]$^+$ Theoretical for $C_{25}H_{25}N_4O_3$: 429.1928; Experimental: 429.1949.

(R)—N-(1-(naphthalen-1-yl)ethyl)-2-(3-oxo-3-(2-propioloylhydrazineyl)propyl)benzamide (12). Compound 12 was synthesized under the same conditions as compounds 7, 9, 11, and 13 except the initial coupling to the hydrazide of 5 was achieved with 3-(trimethylsilyl)propioloyl chloride. The DCM was removed under reduced pressure and the crude material was immediately dissolved in 1:1 THF:MeOH (6 mL total volume) and 10 mg of $K_2CO_3$ was added. The solution was stirred and monitored by TLC until the reaction was complete, approximately 30 min. The solution was concentrated and purified by silica gel flash chromatography (2:1 EtOAc:Hexanes) to yield 8 mg (0.019 mmol, 23%) of a pale yellow solid. $^1$H NMR (500 MHz, Acetone-$d_6$, δ from residual protio solvent) δ 9.49 (s, 1H), 9.12 (s, 1H), 8.33 (d, J=8.6 Hz, 1H), 8.05 (d, J=8.2 Hz, 1H), 7.93 (d, J=8.2 Hz, 1H), 7.83 (d, J=8.2 Hz, 1H), 7.72 (d, J=7.2 Hz, 1H), 7.63 (t, J=7.8 Hz, 1H), 7.52 (m, 2H), 7.40-7.28 (m, 3H), 7.19 (m, 1H), 6.12 (p, J=7.3 Hz, 1H), 3.14-3.00 (m, J=7.4 Hz, 2H), 2.79 (s, 1H), 2.64 (m, 2H), 1.74 (d, J=6.8 Hz, 3H). $^{13}$C NMR (126 MHz, Acetone, δ from solvent) δ 171.42, 169.30, 151.76, 140.76, 140.01, 138.07, 134.97, 132.12, 130.72, 130.42, 129.63, 128.52, 128.23, 127.15, 126.83, 126.52, 126.35, 124.37, 123.62, 79.90, 77.04, 76.70, 45.67, 36.17, 21.58. HRMS-ESI (m/z): [M+H]$^+$ Theoretical for $C_{25}H_{24}N_3O_3$: 414.1819; Experimental: 414.1852.

(R)-2-(3-(2-(2-cyano-3-cyclopropylacryloyl)hydrazineyl)-3-oxopropyl)-N-(1-(naphthalen-1-yl)ethyl)benzamide (13). $^1$H NMR (500 MHz, Acetone-$d_6$, δ from residual protio solvent) δ 8.32 (d, J=8.6 Hz, 1H), 7.99-7.91 (m, 2H), 7.83 (d, J=8.3 Hz, 1H), 7.71-7.68 (m, 2H), 7.63-7.58 (m, 1H), 7.57-7.46 (m, 2H), 7.39 (m, 1H), 7.32 (m, 2H), 7.21 (t, J=7.1 Hz, 1H), 6.10 (p, J=7.5 Hz, 1H), [1:2.5 E:Z isomer ratio; 4.51 (dd, J=25.6, 7.6 Hz), 4.24 (dd, J=54.2, 11.8 Hz, 1H)], 3.21-2.98 (m, 4H), 2.77 (s, 1H), 1.73 (d, J=6.9 Hz, 3H), 1.18-1.02 (m, 1H), 0.70-0.56 (m, 2H), 0.56-0.41 (m, 2H). Many multiple peaks with close 6 spacings were observed in the $^{13}$C NMR presumably due to the E:Z isomer mixture, these values are reported as observed. $^{13}$C NMR (126 MHz, Acetone-$d_6$, δ from solvent) δ 169.39, 169.21, 169.17, 169.15, 169.11, 169.06, 166.20, 166.09, 140.81, 140.80, 140.06, 140.05, 140.03, 139.99, 138.12, 138.09, 134.96, 132.10, 132.08, 131.02, 131.00, 130.47, 130.45, 129.68, 129.65, 128.53, 128.51, 128.50, 128.17, 128.14, 127.12, 127.11, 126.91, 126.51, 126.37, 126.32, 124.33, 124.31, 123.53, 123.49, 123.47, 115.74, 115.72, 114.81, 114.79, 64.23, 59.93, 45.69, 45.65, 45.62, 43.16, 43.13, 43.02, 42.97, 39.15, 39.11, 39.07, 30.30, 30.15, 29.99, 29.84, 29.69, 29.53, 29.38, 29.10, 28.56, 28.54, 21.64, 21.60, 12.09, 12.05, 12.02, 3.47, 3.23, 3.20, 2.90, 2.13, 2.10. HRMS-ESI (m/z): [M+H]$^+$ Theoretical for $C_{29}H_{29}N_4O_3$: 481.2240; Experimental: 481.2289.

Preparation of noncovalent derivatives of GRL0617. Compounds 14 and 15 were prepared analogously to the amide coupling of 3. The amount of materials used were: 2-methylbenzoic acid (0.250 g, 1.80 mmol); 5-acetamido-2-methylbenzoic acid (0.348 g, 1.80 mmol); HBTU (0.853 g, 2.25 mmol); (R)-1-(naphthalen-1-yl)ethan-1-amine (0.306 g, 1.80 mmol) and DIPEA (0.392 mL, 2.25 mmol). Silica gel column purification was performed on 14 (3:1 Hexanes:EtOAc) and 15 (5% MeOH in DCM) to yield white solids 14 (0.463 g, 1.61 mmol, 89%); 15 (0.519 g, 1.50 mmol, 83%).

(R)-2-methyl-N-(1-(naphthalen-1-yl)ethyl)benzamide (14). $^1$H NMR (500 MHz, DMSO-$d_6$, δ from residual protio solvent) δ 8.86 (d, J=8.0 Hz, 1H), 8.25 (d, J=8.4 Hz, 1H), 7.96 (d, J=8.0 Hz, 1H), 7.85 (d, J=8.1 Hz, 1H), 7.66-7.49 (m, 4H), 7.35-7.28 (m, 2H), 7.25-7.19 (m, 2H), 5.93 (p, J=7.2 Hz, 1H), 2.30 (s, 3H), 1.59 (d, J=6.9 Hz, 3H). $^{13}$C NMR (126 MHz, DMSO, δ from solvent)) δ 168.09, 140.25, 137.22, 135.01, 133.35, 130.40, 130.23, 129.07, 128.62, 127.18, 126.96, 126.08, 125.55, 125.43, 125.36, 123.17, 122.49, 44.26, 21.42, 19.21. HRMS-ESI (m/z): [M+H]$^+$ Theoretical for $C_{20}H_{20}NO$: 290.1545; Experimental: 290.1594.

(R)-5-acetamido-2-methyl-N-(1-(naphthalen-1-yl)ethyl)benzamide (15). $^1$H NMR (500 MHz, DMSO-$d_6$, δ from residual protio solvent) δ 9.91 (s, 1H), 8.85 (d, J=8.1 Hz, 1H), 8.24 (d, J=8.5 Hz, 1H), 7.96 (dd, J=8.1, 1.6 Hz, 1H), 7.84 (d, J=8.2 Hz, 1H), 7.64-7.45 (m, 7H), 7.12 (d, J=8.3 Hz, 1H), 5.92 (p, J=7.1 Hz, 1H), 3.29 (s, 1H), 2.69 (s with broadened couplings, 3H), 2.21 (s, 3H), 2.01 (d, J=1.7 Hz, 3H), 1.57 (d, J=6.9 Hz, 3H), 1.19 (s, 1H). $^{13}$C NMR (126 MHz, DMSO, δ from solvent) δ 168.12, 167.96, 140.20, 137.52, 136.78, 133.33, 130.40, 130.38, 129.10, 128.59, 127.18, 126.10, 125.55, 125.37, 123.15, 122.42, 119.51, 117.50, 44.15, 38.19, 23.84, 21.44, 18.51. HRMS-ESI (m/z): [M+H]$^+$ Theoretical for $C_{22}H_{23}N_2O_2$: 369.1579; Experimental: 369.1555.

Protein expression and purification. PLpro from SARS-CoV-2 was produced using a previously described procedure (W. C. Leite et al., J. Phys. Chem. Lett., 12(23), 5608-5615, 2021), but with minor modifications. The procedure is summarized as follows. First, the protein was expressed using E. coli BL21(DE3) cells that had been transformed with a pMCSG92 expression plasmid, which includes a T7 promoter and TEV protease-cleavable C-terminal 6×His tag. Cells were plated on LB agar and cultivated in a shaking incubator (250 rpm) at 37° C. in Lysogeny Broth medium (Lennox recipe) using 1 L per baffled 2.8 L Fernbach flask. Carbenicillin was used for antibiotic selection throughout. Bacterial growth was monitored by measuring the absorbance at 600 nm ($OD_{600}$). Upon reaching an $OD_{600}$ of ~0.7, the incubator temperature was set to 18° C. and isopropyl β-D-1-thiogalactopyranoside (IPTG) was added to 0.2 mM. After approximately 18 hours, the culture was harvested by centrifugation at 6000×g for 30 minutes. After decanting off the supernatant, the pellets were stored at −80° C. until needed for protein purification.

A cell pellet harvested from a 1 L culture was thawed and resuspended in 100 mL of lysis buffer containing 50 mM HEPES, 300 mM NaCl, 50 mM imidazole, 5% glycerol, and 1 mM TCEP at pH 7.4. Following resuspension, the cells were subjected to tip sonication on ice at 50% amplitude (2 seconds on and 10 seconds off) for a total sonication time of 5 minutes. After clarifying the lysate by 38,500×g centrifugation for 35 minutes at 4° C., the decanted supernatant was passed through 1.6-micron and 0.45-micron syringe filters sequentially and kept on ice while loading a 5-mL HisTrap HP column (Cytiva) at 2 mL/min. After washing the column with 10 column volumes (CV) of lysis buffer, partially purified PLpro was eluted using a linear gradient (20 CVs) of lysis buffer with 500 mM imidazole. Elution fractions (2 mL) were collected and PLpro was identified using SDS-PAGE on a 4-20% Mini-Protean TGX Stain-Free protein gel (Bio-Rad). Pooled fractions containing PLpro were dialyzed overnight at 6° C. in 50 mM HEPES pH 7.4 with 150 mM NaCl, 5% glycerol, 20 mM imidazole, and 1 mM TCEP in the presence of His-tagged TEV protease (1 mg TEV protease:100 mg PLpro). After confirming His-tag cleavage by SDS-PAGE, the dialyzed protein solution was passed over a 5-mL HisTrap HP column to remove His-tagged impurities. The column flowthrough was collected, evaluated with SDS-PAGE, and concentrated with a 10-kDa molecular weight cutoff Amicon Ultra15 ultrafiltration membrane. Upon concentration, partially purified protein was applied at 0.5 mL/min to a Superdex 75 10/300 GL size-exclusion column that had been equilibrated with 50 mM Tris HEPES pH 7.4 with 150 mM NaCl, 5% glycerol, and 1 mM TCEP. Fractions (0.5 mL) containing purified PLpro were collected, pooled, and concentrated for further use.

PLpro inhibition assays. The assays were performed in 40 μL total volume in black half area 96-well plates (Greiner PN 675076) at 25° C. The assay buffer contained 20 mM Tris-HCl pH 7.45, 0.1 mg/mL bovine serum albumin fraction V, and 2 mM reduced glutathione. The final DMSO concentration in all assays was 2.5% v/v. PLpro initial rates were measured using a previously established fluorogenic peptide substrate assay (e.g., K. Ratia et al., Proc. Natl. Acad. Sci. USA, 105(42), 16119-24, 2008). The substrates Z-LRGG-AMC and Z-RLRGG-AMC were dissolved to 10 mM in DMSO and stored in aliquots at −20° C. To determine Michaelis-Menten parameters, 20 μL enzyme solution was dispensed into wells (250 nM final concentration), and reactions were initiated by adding 20 μL substrate to 0-500 μM final concentration, in triplicate. Release of aminomethylcoumarin (AMC) was monitored by a fluorescence plate reader every 50 s with an excitation wavelength of 345 nm and an emission wavelength of 445 nm, 6.25 mm read height, and gain=60. After background subtraction of the average of no-enzyme negative controls, product formation was quantified using a 0.02-5 μM calibration curve of AMC. Initial rates were determined for time points in the initial linear range by linear regression in Excel, and GraphPad Prism 9 was used to perform nonlinear regression of the Michaelis-Menten equation to the initial rate vs. substrate concentration data to yield $K_M$ and $V_{max}$.

Inhibitors were characterized by dispensing 10 μL enzyme solution into wells (115 nM final concentration), followed by 10 μL inhibitor solution at 4× desired final concentrations in 5% v/v DMSO in at least duplicate, centrifuging briefly, and incubating for 30 min. Reactions were initiated by adding 20 μL substrate to 100 μM final concentration. Initial rates were determined as described above and % residual activities were determined by normalizing to the average of no inhibitor controls (100% activity). Thirty-minute $IC_{50}$ values were determined by nonlinear regression to the [Inhibitor] vs. normalized response-Variable slope equation using GraphPad Prism 9. Results are shown in the table below.

TABLE 2

PLpro Enzyme Inhibition Assay Data

| Compound No. | $IC_{50}$ (μM) |
|---|---|
| 7 | 0.094 |
| 8 | 0.230 |
| 9 | 5.4 |
| 10 | 4.4 |
| 11 | 8.0 |
| 12 | 0.098 |
| 13 | >200 |
| 14 | 100 |
| 15 | 6.2 |

In addition to its role in processing the viral replicase polyprotein, SARS-CoV-2 PLpro displays deubiquitinase and de-ISG15ylase activities toward host proteins (11, 26). To ensure that the most promising covalent inhibitors 7 and 9 can inhibit PLpro-catalyzed cleavage of ubiquitinated and ISGylated substrates, IC50 values were obtained for ubiquitin-rhodamine and ISG15-CHOP2 substrates. Compound 7 inhibited PLpro with ubiquitin-rhodamine and ISG15 substrates with $IC_{50}$ values of 76 and 39 nM, respectively. The corresponding $IC_{50}$ values for 9 with these two substrates were 1.96 and 20.2 μM, respectively.

Inhibition of SARS-CoV-2 Viral Replication

Initial screening to measure cytopathic effect (CPE) protection for the 50% efficacy concentration (EC50) and cytotoxicity (CC50) was performed using an assay based on African green monkey kidney epithelial (Vero E6) cells in 384-well plates (25). Each plate can evaluate 5 compounds in duplicate at 7 concentrations to measure an EC50 and CC50. Each plate included three controls: cells alone (uninfected control), cells with SARS-CoV-2 (infected control) for plate normalization, and remdesivir as a drug control. Cell viability was measured using the CellTiter-Glo Luminescent Cell Viability Assay. In brief, Vero E6 TMPRSS ACE2 cells were grown to ~90% confluency in 384-well plates and treated for 1 hr with selected compounds. Cells were infected at an MOI=0.1 of SARS-CoV-2 isolate USA-WA1/2020 (27). After 48 h, the SARS-CoV-2-mediated CPE or cytotoxicity was assessed by measurement of live cells using CellTiter-Glo. The selectivity index at 50% (SI50) was then calculated from the EC50 and CC50 values. Results are summarized in Table 3 and Table 4.

TABLE 3

Cytopathic Effect Assay Data

| Compound No. | $EC_{50}$ (μM) |
|---|---|
| 7 | 1.1 |
| 8 | no CPE |
| 9 | 34 |
| 10 | no CPE |
| 11 | no CPE |
| 12 | no CPE |
| 13 | no CPE |

TABLE 4

Cytotoxicity Assay Data

| Compound No. | $CC_{50}$ (<30 μM) |
|---|---|
| 7 | no |
| 8 | no |
| 9 | no |
| 10 | no |
| 11 | no |
| 12 | yes |
| 13 | yes |

Deubiquitinase screening was also conducted. Because PLpro bears structural and functional similarity to human DUBs and related enzymes, PLpro inhibitor selectivity is an important safety consideration. Seven human DUBs, UCHL1, USP2, USP4, USP7, USP8, USP15, and USP30, were assayed to determine whether they were inhibited by 7 and 9. For both compounds, no inhibition was observed at concentrations up to 30 μM for the human DUBs. Results are summarized in Table 5 below.

TABLE 5

Biochemical Assay Data

| Compound No. | $IC_{50}$ (μM) values versus seven human deubiquitinases |
|---|---|
| 7 | >30 |
| 9 | >30 |

Time-dependent inhibition assays were performed as described above, except that preincubation times were varied by adding the inhibitor to the enzyme at specific time points. For each inhibitor concentration, initial rates were normalized such that 0 preincubation time is 100% and plotted against preincubation time. A nonlinear regression to a one phase decay model was performed to determine the rate constants $k_{obs}$ for each concentration and their 95% confidence intervals. These rate constants were then plotted against inhibitor concentration, and the data in the initial linear region was fit to determine the slope, which is $k_{inact}/K_I$. All regressions were performed with GraphPad Prism 9.

Inhibition of full-length Nsp3 de-ISG15ylase activities. HEK293T cells were grown in 10 cm dishes and transiently transfected with pEF-HA-Nsp3 or pEF empty vector using lipofectamine 3000. 24 hrs after transfection, cells were harvested and lysed in 1% NP-40 lysis buffer (50 mM Tris-HCl, pH 7.5, 150 mM NaCl, 10% glycerol, 1% NP-40, 1 mM phenylmethylsulfonyl fluoride (PMSF)). Full-length HA-Nsp3 was purified using anti-HA immunoprecipitation, washed 4 times using the lysis buffer and the Nsp3 containing beads (~100 μl bead volume) were resuspended in 1.0 ml enzyme assay buffer (20 mM Tris-HCl, pH 8.0, 0.05% CHAPS, 2 mM β-mercaptoethanol). 20 μl of the immunoprecipitated Nsp3 beads and the whole cell lysates (30 μg) were run on 8% SDS-PAGE, transferred to PVDF membrane, and probed with anti-HA antibody to detect full length Nsp3. Activity of Nsp3 on the bead (5.0 μl) was monitored using ISG15-CHOP2 substrate (20 nM) in the presence of DMSO as vehicle or dose range of compounds in DMSO. Percent inhibition was calculated using the formula, % Inhibition=100×[1−($X$−LOW)/(HIGH−LOW)]

where X is the signal at a given concentration of inhibitor, LOW is the signal with no DUB added (100% inhibition) and HIGH is the signal with DUB in the presence of DMSO (0% inhibition). Percent inhibition was plotted using GraphPad Prism and $IC_{50}$ values were determined using nonlinear regression to the [Inhibitor] vs. normalized response-Variable slope equation using GraphPad Prism 9.

Mass spectrometry to assess covalent adduct formation. An HDMS QTOF mass spectrometer was used to measure the intact protein mass of PLpro with and without preincubation with inhibitors to detect covalent adduct formation. To prepare the samples, 2 L of 20 mM inhibitor stocks in DMSO were added to 100 μL PLpro at 1 mg/mL concentration and incubated 1 h at room temperature. Previously described protocols for ultrafiltration and denaturing direct infusion were implemented as follows. Samples were processed by ultrafiltration with a 10 kDa PES membrane by diluting the sample to 0.5 mL with 10 mM LC-MS grade ammonium acetate and reducing volume to 50 μL twice, followed by the same procedure with 2.5 mM ammonium acetate. Protein concentrations were estimated by A280 with a NanoDrop 2000, and samples were diluted to 2 mg/mL in 2.5 mM ammonium acetate, and then 10 μL were further diluted into 90 μL 50:50 acetonitrile:water with 0.1% formic acid. Sample was introduced into the electrospray ionization source by syringe pump at a flow rate of 10 μL/min and MS1 spectra were collected for m/z 400-1500, 5 s/scan, for 1 min. The protein monoisotopic mass was determined from the averaged spectra using mMass 5.5 (M. Strohalm et al., Anal. Chem., 82(11), 4648-4651, 2010).

Inhibition of PLpro deubiquitinase and de-ISG15ylase activities and deubiquitinase selectivity. Candidate inhibitors were assayed in quadruplicate for inhibition of SARS-CoV-2 PLpro with Ub-rhodamine or ISG15-CHOP2 and with human deubiquitinase (DUB) enzymes, including USP30, USP15, USP8, USP7, USP4, and USP2C as well as UCHL1 with Ub-rhodamine, except for USP7, which was tested with Ub-CHOP2. The CHOP assay uses a quenched enzyme platform to quantify the DUB inhibition activity of the compounds. In this assay, a reporter enzyme is fused to the C-terminus of ubiquitin. The reporter is silent when fused to ubiquitin but becomes fluorescent upon cleavage from the C-terminus by a DUB. Thus, measurement of the reporter activity is a direct measure of DUB activity. Assays were performed with a positive control (PR619) and negative control (i.e., without the inhibitor). DUBs at previously optimized concentrations were used with previously optimized suitable DUB substrates to evaluate inhibitory activity. Briefly, the received compounds in DMSO were thawed before use and simultaneously aliquoted to protect against deterioration from freeze-thaw cycles. Compounds were diluted at desired fold to measure a dose response curve in DMSO. DMSO control was used as 0% inhibition in the presence of DUB and the DMSO control without the DUB was considered as the 100% inhibition control to calculate $IC_{50}$ values. Dose response-inhibition curves were plotted in GraphPad Prism with log-transformed concentration on the X-axis with percentage inhibition (30 min time point) on the Y-axis using log [inhibitor] versus the response-variable slope. The selectivity index (SI) is the fold change in selectivity for PLpro compared to the DUB inhibition activity of other DUBs in the selectivity panel.

PLpro expression, purification, and crystallization. Wild-type PLpro from SARS-CoV-2 was expressed in BL21 (DE3) E. coli cells transformed with the pMCSG53 expression plasmid with a T7 promoter and a TEV-cleavable, N-terminal 6×His-tagged PLpro. E. coli cells were grown in LB media containing 50 μg/mL ampicillin at 37° C. in a shaking incubator (200 rpm) until the optical density ($OD_{600}$) of the culture was 0.6. The culture was then induced with 0.5 mM IPTG and grown for 16 hours at 18° C. The culture was centrifuged for 15 min at 3000×g and the cells were obtained as pellets. E. coli pellets were resuspended in lysis buffer (50 mM HEPES pH 7.2, 150 mM NaCl, 5% glycerol, 20 mM imidazole, 10 mM 2-mercaptoethanol) and subjected to sonication for cell lysis. The soluble fraction of the whole cell lysate was separated by centrifugation at 20442×g for 80 minutes and was loaded onto a Ni-NTA Agarose gravity column pre-equilibrated with lysis buffer. The column was washed with 25 column volumes of wash buffer (50 mM HEPES pH 7.2, 150 mM NaCl, 5% glycerol, 50 mM imidazole, 10 mM 2-mercaptoethanol) and eluted in fractions with elution buffer (50 mM HEPES pH 7.2, 150 mM NaCl, 5% glycerol, 500 mM imidazole, 10 mM 2-mercaptoethanol). Fractions containing PLpro protein as determined by SDS-PAGE were combined and dialyzed overnight in dialysis buffer (50 mM HEPES pH 7.2, 150 mM NaCl, 5% glycerol, 10 mM 2-mercaptoethanol). Dialyzed PLpro was mixed with 6×His-tagged TEV protease in 25:1 ratio, incubated overnight at 4° C. and was passed through Ni-NTA Agarose gravity column pre-equilibrated with dialysis buffer (50 mM HEPES pH 7.2, 150 mM NaCl, 5% glycerol, 10 mM 2-mercaptoethanol) to remove 6×His-tagged impurities and TEV protease. Tagless PLpro obtained as the flowthrough was flash frozen and stored at −80° C. All extraction and purification steps were performed at 4° C. Reaction of tag-less PLpro in 20 mM Tris HCl pH 8.0 and 5 mM NaCl with a 10-fold molar excess of compound 7 was performed at 37° C. for 20 minutes. The PLpro-compound 7 complex in a solution containing 20 mM Tris HCl, 100 mM NaCl and 10 mM DTT was then used for crystallization at a concentration of 8 mg/ml. Initial crystal hits were obtained by screening around 900 crystallization conditions by the sitting drop method. Diffraction-quality crystals were obtained from a well solution containing PEG-3350, $CaCl_2$), $CdCl_2$ and $CoCl_3$.

Data collection and structure determination. The diffraction data were collected at 100 K at the BL12-2 beamline of the Stanford Synchrotron Radiation Light Source using Pilatus 6M detectors. Crystals for the complex were cryo-cooled using the well solution supplemented with 20% ethylene glycol. Diffraction data from two crystals were collected with 360 degrees of data per crystal and 0.2 degrees oscillation per image. For each crystal, diffraction data were merged and processed with the XDS suite of programs. The structures were solved by molecular replacement with AMoRE using the coordinates of SARS-CoV-2 PLpro complexed with the tetrapeptide-based inhibitor VIR251 (PDB 6WX4) as the search model. Iterative rounds of model building and refinement were performed with the programs COOT and REFMAC.

SARS-CoV-2 antiviral assays. Initial screening to measure cytopathic effect (CPE) protection for the 50% efficacy concentration ($EC_{50}$) and cytotoxicity ($CC_{50}$) was performed using an assay based on African green monkey kidney epithelial (Vero E6) cells in 384-well plates. Each plate can evaluate five compounds in duplicate at seven concentrations to measure an $EC_{50}$ and $CC_{50}$. Each plate included three controls: cells alone (uninfected control), cells with SARS-CoV-2 (infected control) for plate normalization, and remdesivir as a drug control. Cell viability was measured using the CellTiter-Glo Luminescent Cell Viability Assay. In brief, Vero E6 TMPRSS ACE2 cells were grown to ~90% confluency in 384-well plates and treated for 1 hr with compounds. Cells were infected at an MOI=0.1 of SARS-CoV-2 isolate USA-WA1/2020. After 48 h, the SARS-CoV-2-mediated CPE and cytotoxicity were assessed by measuring live cells using CellTiter-Glo. The selectivity index at 50% ($SI_{50}$) was then calculated from the $EC_{50}$ and $CC_{50}$ values. To ensure robust and reproducible signals, each 384-well plate was evaluated for its Z-score, signal to noise, signal to background, and coefficient of variation. This assay has been validated for use in high-throughput format for single-dose screening and is sensitive and robust, with Z values >0.5, signal to background >20, and signal to noise >3.3. Antiviral activity and cytotoxicity were also assessed with compound in the presence of 2 μM CP-100356 and SARS-CoV-2. Following incubation for 48 hours at 5% $CO_2$ and 37° C., the percent cell viability was measured with CellTiterGlo. Signals were read with a multimode plate reader. Cells alone (positive control) and cells plus virus (negative control) were set to 100% and 0% cell viability to normalize the data from the compound testing. Data were normalized to cells (100%) and virus (0%) plus cells. Each concentration was tested in duplicate.

Compounds were also tested against SARS-CoV-2 variants using Vero E6 cells using methods described previously (H. Liu et al., Nat. Commun. 13(1), 1891, 2022). Confluent or near-confluent cell culture monolayers of Vero E6 cells were prepared in 96-well disposable microplates the day before testing. Cells were maintained in Modified Eagle Medium (MEM) supplemented with 5% fetal bovine serum (FBS). For antiviral assays the same medium was used but with FBS reduced to 2% and supplemented with 50 μg/ml gentamicin. Compounds were dissolved in DMSO, saline, or the diluent requested by the submitter. Less soluble compounds were vortexed, heated, and sonicated, and, if they still did not go into solution, were tested as colloidal suspensions. Each test compound was prepared at four serial $log_{10}$ concentrations, usually 0.1, 1.0, 10, and 100 μg/ml or μM (per sponsor preference). Lower concentrations were used when insufficient compound was supplied. Five microwells were used per dilution: three for infected cultures and two for uninfected toxicity cultures. Controls for the experiment consisted of six microwells that were infected and not treated (virus controls) and six that were untreated and uninfected (cell controls) on every plate. A known active drug was tested in parallel as a positive control drug using the same method applied for test compounds. The positive control was tested with every test run.

Growth media was removed from the cells and the test compound was applied in 0.1 ml volume to wells at 2× concentration. Virus, normally at ~60 $CCID_{50}$ (50% cell culture infectious dose) in 0.1 ml volume, was added to the wells designated for virus infection. Medium devoid of virus was placed in toxicity control wells and cell control wells. Plates were incubated at 37° C. with 5% $CO_2$ until marked CPE (>80% CPE for most virus strains) was observed in virus control wells. The plates were then stained with 0.011% neutral red for approximately two hours at 37° C. in a 5% $CO_2$ incubator. The neutral red medium was removed by complete aspiration, and the cells were rinsed 1× with phosphate buffered saline (PBS) to remove residual dye. The PBS was removed completely, and the incorporated neutral red was eluted with 50% Sorensen's citrate buffer/50% ethanol for at least 30 minutes. Neutral red dye penetrates living cells. Thus, the more intense the red color, the larger the number of viable cells are present in the wells. The dye content in each well was quantified using a spectrophotometer at 540 nm wavelength. The dye content in each set of wells was converted to a percentage of dye present in untreated control wells using a Microsoft Excel spreadsheet and normalized based on the virus control. The 50% effective $EC_{50}$ concentrations and 50% cytotoxic ($CC_{50}$) concentrations were then calculated by regression analysis. The quotient of $CC_{50}$ divided by $EC_{50}$ gives the selectivity index (SI). Compounds showing SI values >10 were considered active.

To confirm antiviral activity of compounds in human cells, the compounds were evaluated against SARS-CoV2 variants using a Caco-2 virus yield reduction assay. Briefly, near-confluent monolayers of Caco-2 cells were prepared in 96-well microplates the day before testing. Cells were maintained in MEM supplemented with 5% FBS. The test compounds were prepared at a serial dilution of concentrations. The antiviral activity was also assessed with the compound alone or in the presence of 2 µM CP-100356. Three microwells were used per dilution. Controls for the experiment consisted of six microwells that were infected and not treated (virus controls) and six that were untreated and uninfected (cell controls) on every plate. A known active drug was tested in parallel as a positive control drug using the same method as is applied for test compounds. The positive control was tested with every test run. Growth media was removed from the cells and the test compound applied in 0.1 ml volume to wells at 2× concentration. Virus, normally at ~60 $CCID_{50}$ (50% cell culture infectious dose) in 0.1 ml volume, was added to the wells designated for virus infection. Medium devoid of virus was placed in cell control wells. Plates were incubated at 37° C. with 5% $CO_2$. After sufficient virus replication occurs (3 days for SARS-CoV-2), a sample of supernatant was taken from each infected well (three replicate wells were pooled) and tested immediately for virus yield reduction (VYR) or held frozen at −80° C. for later virus titer determination.

The VYR test is a direct determination of how much the test compound inhibits virus replication. Virus yielded in the presence of test compound was titrated and compared to virus titers from the untreated virus controls. Titration of the viral samples (collected as described above) was performed by endpoint dilution. Serial 1/10 dilutions of virus were made and plated into four replicate wells containing fresh cell monolayers of Vero E6 cells. Plates were then incubated, and cells were scored for the presence or absence of virus after distinct CPE was observed, and the $CCID_{50}$ was calculated using the Reed-Muench method (G. N. Mushudov et al., Acta Crystallogr D Biol Crystallogr, 1997, 53 (Pt 3), 240-55). The 90% effective concentration ($EC_{90}$) was calculated by regression analysis by plotting the $\log_{10}$ of the inhibitor concentration versus $\log_{10}$ of virus produced at each concentration. $EC_{90}$ values were calculated from data to compare to the concentration of drug compounds as measured in the pharmacokinetic experiments. Drug concentrations in critical tissues above $EC_{90}$ values were targeted (instead of $EC_{50}$ values) as for clinically relevant applications.

Metabolic stability. Intrinsic clearance in human, Sprague-Dawley rat, and CD-1 mouse liver microsomes and S9 fractions were measured in duplicate for compounds 7, 9, and 14 by Eurofins Panlabs. Imipramine, propranolol, terfenadine, and verapamil were used as reference compounds at a test concentration of 0.1 µM. In each experiment, and if applicable, the respective reference compounds were tested concurrently with the test compounds, and the data were compared with historical values determined at Eurofins. The experiments were accepted in accordance with Eurofins validation Standard Operating Procedure. Metabolic stability, expressed as percent of the parent compound remaining, was calculated by comparing the peak area of the compound at the time point relative to that at time to. The concentration of each compound was 1 µM and the incubation time ranged from 0 to 60 min. The half-life ($T_{1/2}$) was estimated from the slope of the initial linear range of the logarithmic curve of compound remaining (%) versus time, assuming first-order kinetics. The apparent intrinsic clearance ($CL_{int}$, µL/min/mg) was then calculated according to the following formula:

$$CL_{int} = \frac{0.693}{T_{1/2}\left(mg\frac{protein}{\mu L}\right)}$$

Pharmacokinetics. PK profiling assays were performed. Compound 7 was formulated in 10% dimethyl sulfoxide (DMSO)/30% polyethylene glycol (PEG) 400/10% Kolliphor® EL/50% water for injection (WFI) at 1 and 0.6 mg/mL for PO and IV, respectively. A dosing volume of 10 mL/kg was applied for PO and 5 mL/kg for IV. Male ICR mice weighing 22±2 g were used. Animals were acclimated for 3 days prior to use and were confirmed with good health. All animals were maintained in a hygienic environment with controlled temperature (20-24° C.), humidity (30-70%) and 12 hours light/dark cycles. Free access to sterilized standard lab diet and autoclaved tap water were granted. All aspects of this work, including housing, experimentation, and disposal of animals were performed in general accordance with the Guide for the Care and Use of Laboratory Animals: Eighth Edition (National Academy Press, Washington, D.C., 2011) in an AAALAC-accredited laboratory animal facility. The animal care and use protocol was reviewed and approved by the IACUC at Pharmacology Discovery Services Taiwan, Ltd. Animals were euthanized by $CO_2$ for blood collection by cardiac puncture. Blood samples (300-400 µL) were collected in tubes coated with EDTA-K2, mixed gently, then kept on ice and centrifuged at 2,500×g for 15 minutes at 4° C., within 1 hour of collection. The plasma was then harvested and kept frozen at −70° C. until further processing.

The exposure levels (ng/mL) of 7 in plasma samples were determined by LC-MS/MS. Plots of plasma concentrations (mean±SD) vs. time for 7 were constructed. The fundamental PK parameters after PO ($t_{1/2}$, $T_{max}$, $C_{max}$, $AUC_{last}$, $AUC_{Inf}$, AUC/D, $AUC_{extr}$, MRT, $V_z$, and Cl) and IV ($t_{1/2}$, $C_0$, $AUC_{last}$, $AUC_{Inf}$, AUC/D, $AUC_{extr}$, MRT, $V_{ss}$, and Cl) administrations were obtained from the noncompartmental analysis of the plasma data using WinNonlin (best-fit mode). The mean values of the data at each time point were used in the parameter analysis.

COVID-19 Virus Overview

COVID-19 emerged globally with the rapid spread of the previously unrecognized beta-coronavirus SARS-CoV-2. The virus is highly transmissible and can lead to severe, and in many cases life-threatening, respiratory disease. Few effective drugs have been developed to date, with molnupiravir and nirmatrelvir being the only currently available oral antivirals for treating SARS-CoV-2 infections. Although vaccines and therapeutic antibodies are effective in preventing COVID-19 or reducing its severity, respectively, the emergence of some variants of concern (i.e., Omicron) limits their effectiveness. Thus, there is an urgent need to develop antiviral therapeutics that are effective against SARS-CoV-2 and related coronaviruses.

The SARS-CoV-2 genome encodes two cysteine proteases, the 3-chymotrypsin-like protease (3CLPro or Mpro)

and the papain-like protease (PLpro), both of which are essential for viral maturation. PLpro is a 35-kDa domain of Nsp3, a 215-kDa multidomain protein that is key to maturation of the viral replicase-transcriptase complex (RTC)(J. Lei et al., *Antiviral Res.*, 149, 56-74, 2018). PLpro cleaves the viral polyproteins pp1a and pp1ab at three sites to produce nonstructural proteins Nsp1, Nsp2, and Nsp3. In addition to RTC maturation, PLpro permits evasion of the host immune response by cleaving ubiquitin and the ubiquitin-like protein ISG15 from host protein conjugates (N. Barretto et al., *J Virol* 2005, 79 (24), 15189-98). Compared to PLpro from SARS-CoV (SARS-CoV PLpro), SARS-CoV-2 PLpro displays decreased deubiquitinase activity and enhanced deISGylation activity (B. T. Freitas et al., *CS Infect Dis* 2020, 6 (8), 2099-2109). In addition, PLpro attenuates type I interferon pathways involved in mediating antiviral immune responses (D. Shin et al., Nature, 2020, doi:10.1038/s41586-020-2601-5). Inhibition of SARS-CoV-2 PLpro was shown to reduce viral replication in Vero CCL-81 cells and to maintain the host interferon pathway (D. Shin et al., Ibid.; and T. Klemm et al., *EMBO J* 2020, e106275. doi:10.15252/embj.2020106275).

Figures 2A, 2B:
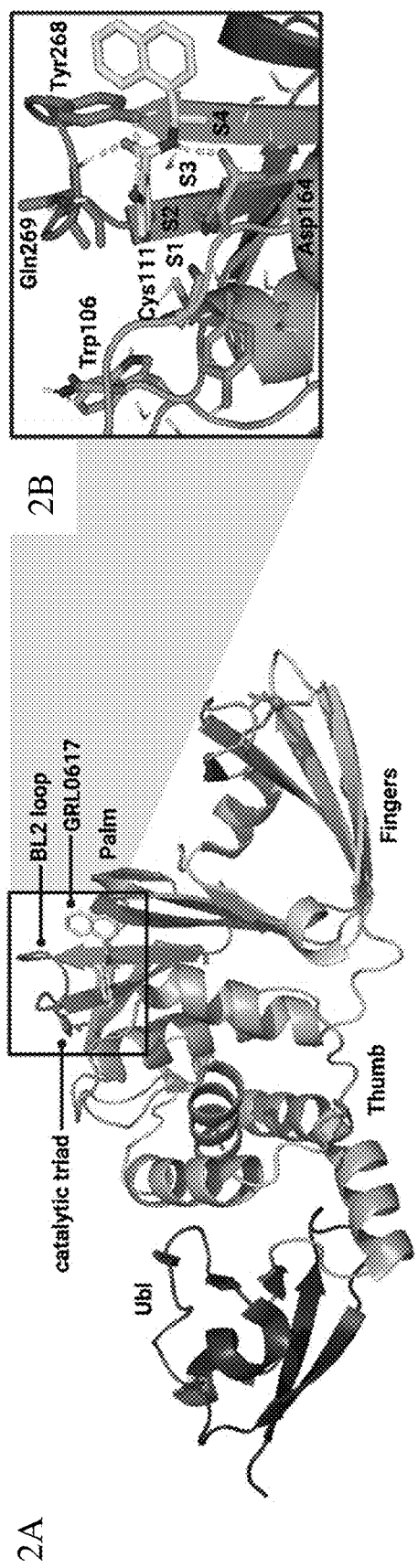
FIGS. 2A-2B.
Figures 3A, 3B, 3C, 3D:
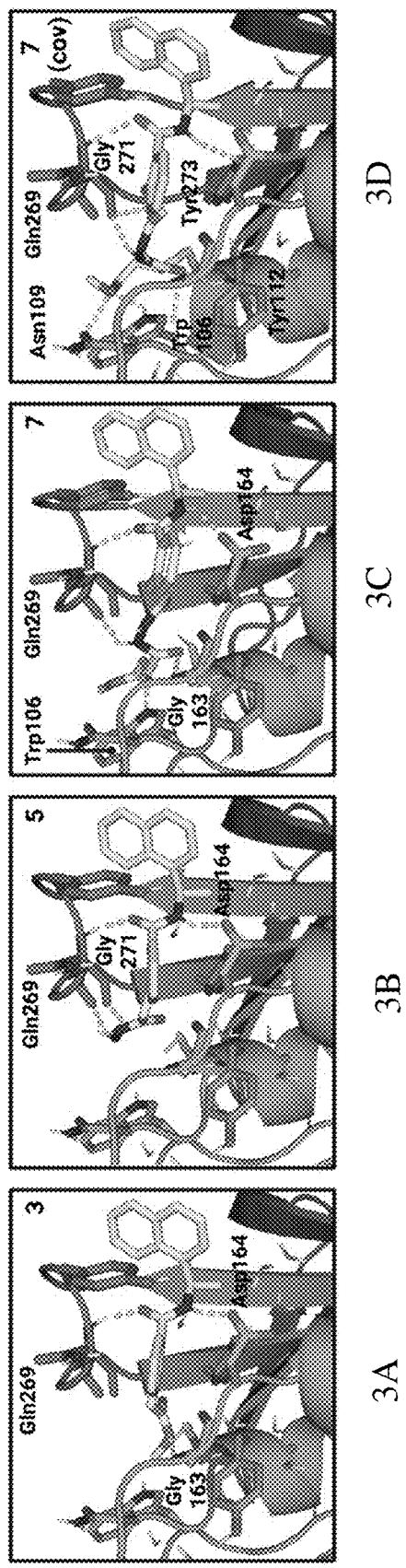
FIGS. 3A-3D (left to right). Docked poses of compound 3 (FIG. 3A), compound 5 (FIG. 3B), and compound 7 docked both noncovalently and covalently (FIGS. 3C and 3D, respectively). Structures of compounds are shown in FIG. 4. Polar hydrogens have been added. Ligand carbons are shown in gray and predicted protein-ligand interactions are shown as dashed yellow lines.

PLpro consists of thumb, fingers, and palm subdomains common to other ubiquitin-specific proteases, and an N-terminal ubiquitin-like domain involved in substrate recognition (FIG. 2A). The active site, which is located at the interface of the thumb and palm subdomains, consists of a catalytic triad comprising Cys111, His272, and Asp286 (T. Klemm et al., Ibid.). Besides the catalytic Cys111, four Cys residues coordinate a structural $Zn^{2+}$ cation in the fingers subdomain and six additional Cys residues are present elsewhere in the protein. Of all the cysteines in PLpro, Cys111 is the most prone to oxidation, indicating that it is unique in its reactivity toward electrophiles (J. Osipiuk et al., *Nat Commun* 2021, 12 (1), 743).

Protein substrates of PLpro consist of a Leu-X-Gly-Gly peptide motif (X=Arg, Lys, or Asn), with proteolytic cleavage occurring after the second Gly residue (N. Barretto et al., Ibid.). Leu and X occupy the S4 and S3 subsites, respectively, and the two Gly residues occupy the S2 and S1 subsites, which are covered by a β-hairpin "blocking loop" (BL2 loop) that forms a narrow groove leading to the active site (FIGS. 2A and 2B) (T. Klemm et al., Ibid.). As a result, only extended peptide substrates with two Gly residues at the P1 and P2 positions can be accommodated in this space (W. Rut et al., *Science Advances*, 6(42), 2020).

Several noncovalent inhibitors of PLpro have been developed that competitively inhibit PLpro (J. Osipiuk et al., Ibid.). The naphthylmethylamine compound GRL0617 inhibits SARS-CoV PLpro with an $IC_{50}$ of ~0.6 µM and inhibits viral replication in Vero E6 cells with $EC_{50}$=14.5 µM (K. Ratia et al., Ibid.). The desamino analog of GRL0617 exhibits similar inhibitory activity ($IC_{50}$=2.3 µM; $EC_{50}$=10 µM), as does the N-acetylated analog ($IC_{50}$=2.6 µM; $EC_{50}$=13.1 µM). GRL0617 exhibits similar inhibition activity against SARS-CoV-2 PLpro (e.g., D. Shin et al., Ibid.). Importantly, GRL0617 does not inhibit the structurally similar human deubiquitinases (DUBs). The $IC_{50}$ values for GRL0617 toward HAUSP, the deISGylase USP18, and the ubiquitin C-terminal hydrolases UCH-L1 and UCH-L3 are all >100 µM (K. Ratia et al., Ibid.). In addition, GRL0617 does not display cytotoxicity at concentrations up to 50 µM in cell viability assays. Crystallographic studies (J. Osipiuk et al., Ibid.) have revealed key interactions between PLpro and GRL0617 including (i) a hydrogen bond between the backbone N—H of Gln269 and the amide carbonyl of the inhibitor, (ii) a hydrogen bond between the N—H of the GRL0617 amide and the carboxylate side chain of Asp164, and (iii) an edge-to-face interaction of the naphthyl group of GRL0617 and Tyr268 (FIG. 2B).

The present work reports in vitro inhibition ($IC_{50}$, $k_{inact}/K_I$), cytopathic protection ($EC_{50}$, $EC_{90}$) and cytotoxicity ($CC_{50}$), electrospray ionization mass spectrometry, X-ray crystallography, enzyme selectivity, metabolic stability, and pharmacokinetics data. The present works shows that the most promising candidate is a highly potent and selective covalent inhibitor of PLpro from SARS-CoV-2.

Design of PLpro Inhibitors

The present work designed a series of covalent PLpro inhibitors based on the noncovalent inhibitor GRL0617. Previous crystallographic studies have revealed that the phenylmethyl group of GRL0617 points toward the active site but is located >7 Å from Sγ of Cys111 (FIG. 2B) (J. Osipiuk et al., Ibid.). In the present work, the phenyl methyl substituent of GRL0617 was replaced with a hydrolytically stable linker connected to an electrophile capable of reacting with Cys111 would yield a potent covalent inhibitor of PLpro. An N,N'-acetylacetohydrazine linker was chosen as a linear Gly-Gly peptidomimetic that could reach through the narrow S2 and S1 groove to the active site while also preserving some of the hydrogen-bonding interactions (e.g., with Gly163 and Gly271) afforded by natural peptide substrates. To the resulting linker was appended a series of electrophiles including a fumarate methyl ester, chloroacetamide, propiolamide, cyanoacetamide, and α-cyanoacrylamide.

To help prioritize designed molecules for synthesis and testing, covalent docking was performed for each candidate molecule to PLpro (FIGS. 3A-3D). Each molecule was also docked non-covalently to assess the favorability of pre-covalent binding. An ensemble of 50 structural models derived from X-ray crystallographic data was used to account for protein flexibility and included selected crystallographic waters during docking, including those that are known to remain stably bound in the S4 subsite in the presence of noncovalent inhibitors. All candidate inhibitors contained the naphthylmethylamine core of GRL0617. To assess pose similarity, the maximum common substructure RMSD (MCS-RMSD) was measured between the docked poses of the candidate inhibitors and the crystallographic pose of GRL0617. In general, the core of the inhibitor designs and their noncovalent precursors reproduced the binding mode of GRL0617 to within 2 Å RMSD, maintaining interactions with Asp164, Tyr268, and Gln269 while the linker simultaneously occupied the S2 and S1 subsites to place the electrophilic group near the catalytic Cys111 nucleophile (FIGS. 3A-3D). Compounds were prioritized for synthesis based on low MCS-RMSD values (≤2 Å), favorable noncovalent and covalent docking scores, and synthetic tractability.

Figure 4:
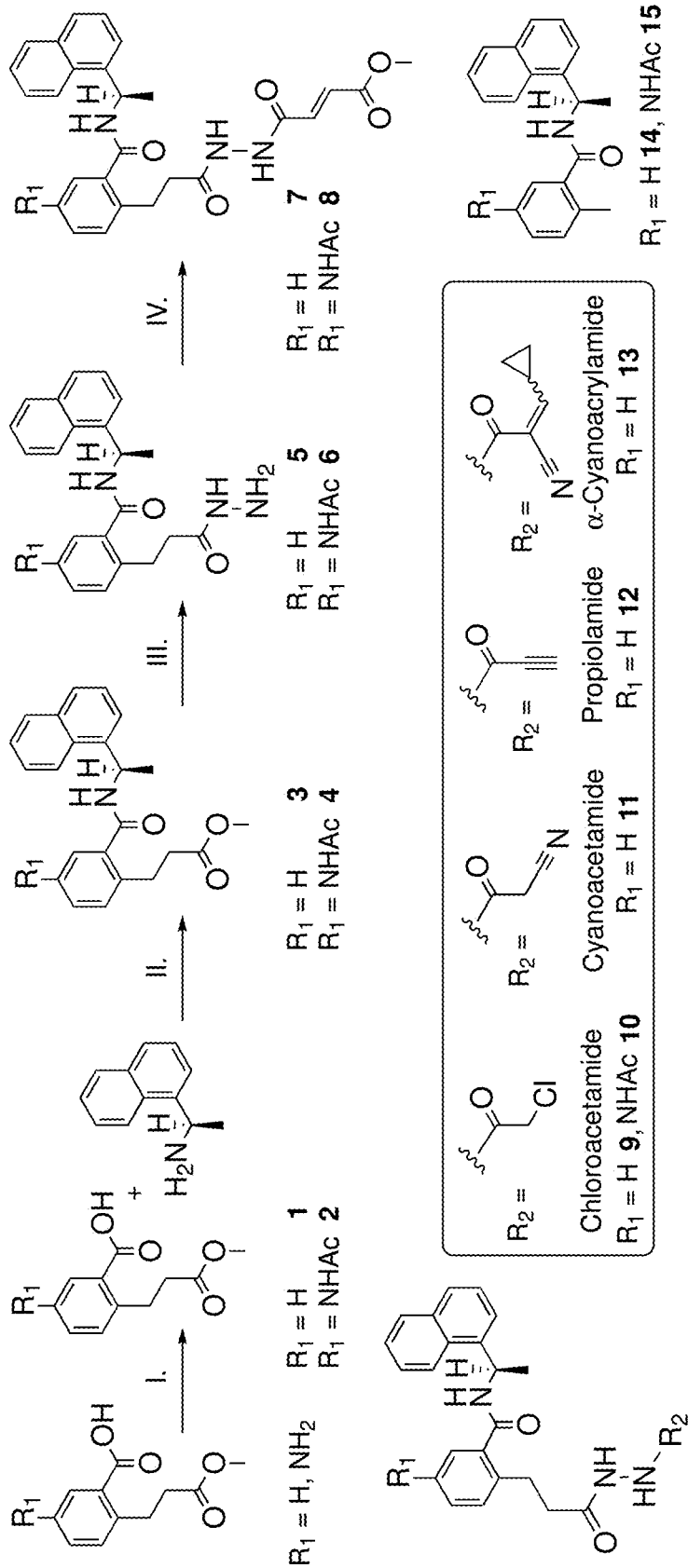
FIG. 4. Schematic showing synthesis of compounds 2-15. Reaction conditions with yields in parentheses: I. Ac$_2$O, AcOH, DCM, 55%; II. HATU, DIPEA, DCM (3, 83%; 4, 91%); III. N$_2$H$_4$.H$_2$O, EtOH (5 and 6, 97%); IV. methyl (E)-4-chloro-4-oxobut-2-enoate, DIPEA, DCM for 7 (56%), and K$_2$CO$_3$, DMF for 8 (34%). Compounds 9 (50%), 10 (37%), 11 (56%), 12 (23%), and 13 (60%) were prepared with the corresponding acid chlorides under conditions described for step IV. Compounds 14 (89%) and 15 (83%) were prepared analogously to step II with 2-methylbenzoic acid and 5-acetamido-2-methylbenzoic acid, respectively.

Compounds 2-15 were synthesized through a straightforward approach beginning from an amide coupling of (R)-(+)-1-(1-napthyl)ethylamine and 2-(3-methoxy-3-oxopropyl)benzoic acid derivatives, where $R_1$=H or NHAc (scheme in FIG. 4). Following this coupling, the ester in 3 and 4 was reacted with $N_2H_4 \cdot H_2O$ in refluxing EtOH to afford the hydrazide group in 5 and 6 in near quantitative yield. With the respective hydrazides in hand, a variety of electrophiles were installed using acid chlorides. Notably, the solubility of 5 and 6 were dramatically different from each other and required separate conditions for installation of the electrophilic groups. DIPEA/DCM was used for 5 ($R_1$=H) and K$_2$CO$_3$/DMF was used for 6 (R$_1$=NHAc). Overall, seven potential covalent inhibitors (7-13) and two additional noncovalent GRL0617 derivatives, namely compounds 14 (R$_1$=H) and 15 (R$_1$=NHAc) were synthesized.

The synthesized compounds were then assessed for potential anti-SARS-CoV-2 activity in a biochemical assay using purified PLpro and a ubiquitin C-terminus-derived fluorogenic substrate Z-RLRGG-AMC (K. Ratia et al., Ibid.). IC$_{50}$ values were determined following a 30-minute incubation of PLpro with inhibitor. Of the noncovalent analogs of GRL0617, it was herein found that both 14 and 15 had increased IC$_{50}$ values, with the N-acetylated compound 15 having an IC$_{50}$ more like that of GRL0617 (Table 6). Encouragingly, extending the tolyl methyl to include a substantially larger peptidomimetic group maintained potency. For example, addition of the linker alone without an electrophile to form 5 led to an IC$_{50}$ of 24 µM (FIG. 4). The introduction of five different electrophilic groups to produce compounds 7, 9, and 11-13 resulted in improved IC$_{50}$ values for all except α-cyanoacrylamide 13. Time-dependent inhibition assays were performed because time-dependence is consistent with multiple mechanisms of slow-binding inhibition, including covalent inhibition via bond formation between Cys111 and the electrophile. Installation of a chloroacetamide electrophile to form 9 improved the IC$_{50}$ compared to 5 to 5.4 µM after 30-min incubation and resulted in a k$_{inact}$/K$_I$ of 100 M$^{-1}$ s$^{-1}$, where k$_{inact}$/K$_I$ is a second-order rate constant describing the efficiency of the overall conversion of free enzyme to the covalent enzyme-inhibitor complex (J. M. Strelow et al., SLAS Discov. 22(1), 3-20, 2017). Similarly, the IC$_{50}$ and k$_{inact}$/K$_I$ for N-acetylated analog 10 are 4.4 µM and 120 M$^{-1}$ s$^{-1}$, respectively.

Discussion

Figures 5A, 5B, 5C, 5D:
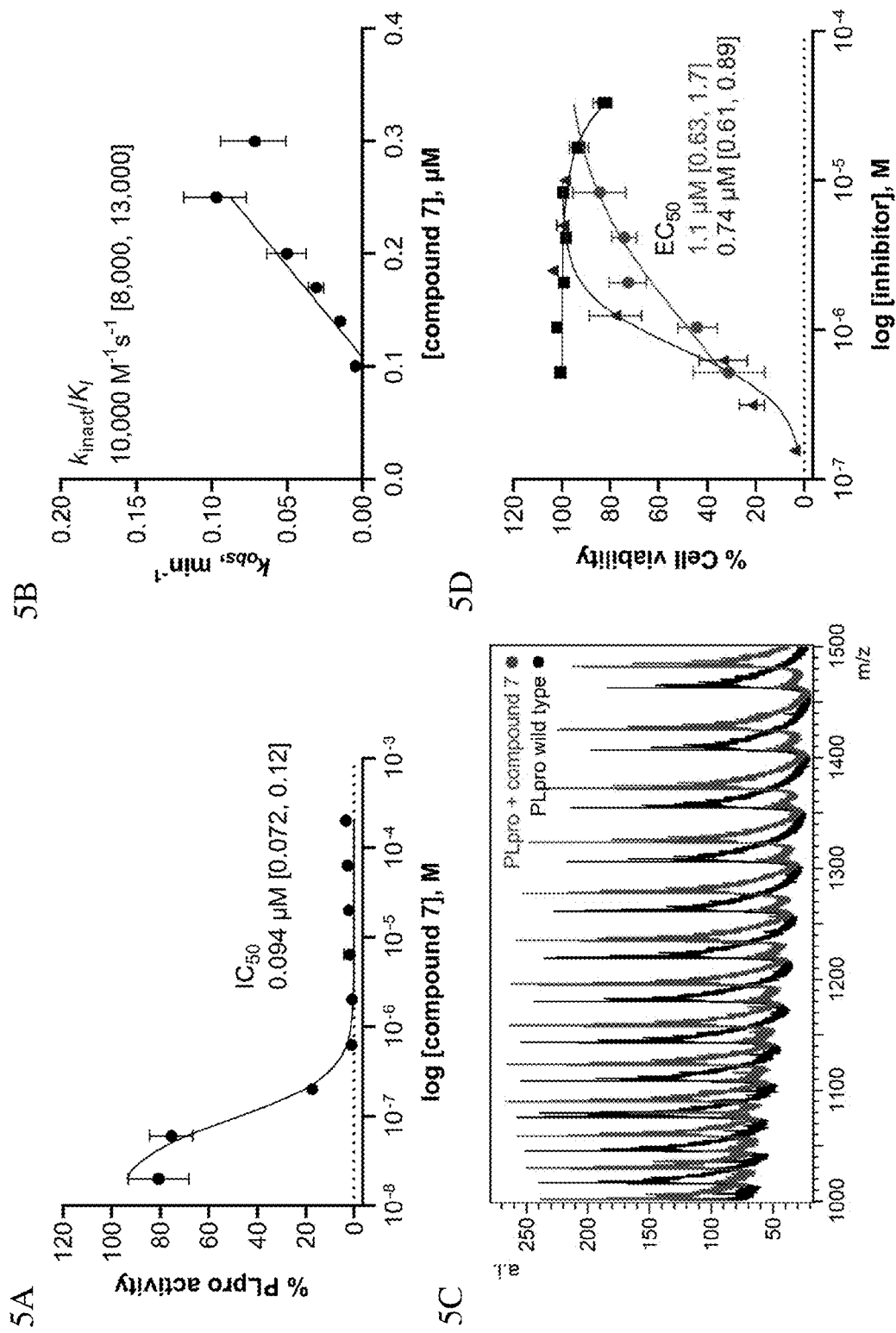
FIGS. 5A-5D. Characterization of a designed covalent PLpro inhibitor, compound 7.

Fumarate methyl ester 7 had an IC$_{50}$ of 94 nM after 30-minute incubation and k$_{inact}$/K$_I$=10,000 M$^{-1}$ s$^{-1}$, indicating potent inhibition (FIG. 5A-B and Table 6). N-acetylated analog 8 showed similar potency, with IC$_{50}$ and k$_{inact}$/K$_I$=230 nM and 14,000 M$^{-1}$ s$^{-1}$, respectively. To examine the inhibitory activity of other electrophiles, time-independent inhibition assays with cyanoacetamide 11 (IC$_{50}$, 8 µM), propiolamide 12 (98 nM), and α-cyanoacrylamide 13 (>200 µM) were performed. Time-dependent inhibition was observed for 12, but not for 11 or 13. To provide additional evidence for a covalent mechanism of action, compounds 7-10 and 12 were incubated with PLpro, and the protein intact masses were determined by electrospray ionization mass spectrometry (ESI-MS). Covalent adduct formation with PLpro was confirmed for these five compounds (FIG. 5C).

TABLE 6

PLpro inhibition and SARS-CoV-2 antiviral activity

| Compound | R$_1$[a] | Electrophile | IC$_{50}$ (µM)[b] | Time dep. | k$_{inact}$/K$_I$ (M$^{-1}$ s$^{-1}$) | EC$_{50}$ (µM)[c] | Cytotox. (<30 µM) |
|---|---|---|---|---|---|---|---|
| GRL0617 | NH$_2$ | NA | 1.2 | no | NA | ND | ND |
| 3 | H | NA | >100 | no | NA | ND | ND |
| 5 | H | NA | 24 | no | NA | ND | ND |
| 7 | H | fumarate ester | 0.094 | yes | 10,000 | 1.1 | no |
| 8 | NHAc | fumarate ester | 0.230 | yes | 14,000 | no CPE | no |
| 9 | H | chloroacetamide | 5.4 | yes | 103 | 34 | no |
| 10 | NHAc | chloroacetamide | 4.4 | yes | 120 | no CPE | no |
| 11 | H | cyanoacetamide | 8.0 | no | ND | no CPE | no |
| 12 | H | propiolamide | 0.098 | yes | 4,800 | no CPE | yes |
| 13 | H | α-cyanoacrylamide | >200 | no | ND | no CPE | yes |
| 14 | H | NA | 100 | ND | NA | no CPE | no |
| 15 | NHAc | NA | 6.2 | ND | NA | no CPE | no |

[a]Structures of compounds 7-13 are shown in Table 1.
[b]Measurement after 30-minute incubation.
[c]Cytopathic effect in SARS-CoV-2-infected Vero E6 cells. EC$_{50}$ for remdesivir = 0.74 µM.
NA = not applicable; ND = not determined.

Next, the ability of selected inhibitors to protect Vero E6 cells from virus-induced cell death, represented by EC$_{50}$ (FIG. 5D), was assessed by incubating cells with and without compound and then infecting them with SARS-CoV-2 (W. E. Severson et al., J. Biomol. Screen, 12(1), 33-40, 2007). Uninfected cells were used to assess the cytotoxicity of the compounds, represented by CC$_{50}$. Compound 7 displayed notable antiviral activity with an EC$_{50}$ of 1.1 µM, comparable to that of the remdesivir positive control (0.74 µM). Chloroacetamide 9 also displayed antiviral activity, although with less potency (34 µM). Neither 7 nor 9 displayed evidence of cytotoxicity (CC$_{50}$>30 mM). Compounds 8 and 10, which have N-acetylated phenyl substituents, showed insignificant cytoprotective effects. Both 12 and 13 were cytotoxic with CC$_{50}$ values of 1-5 µM, suggesting that propiolamide and α-cyanoacrylamide electrophiles were too reactive, lack specificity, or both.

In addition to its role in processing the replicase polyprotein, SARS-CoV-2 PLpro displays deubiquitinase and de-ISG15ylase activity (C. D. Swaim et al., Cell Rep. 31(11), 107772, 2020). To ensure that the most promising covalent inhibitors, 7 and 9, can inhibit these physiologically relevant activities, IC$_{50}$ values were obtained with Ub-rhodamine and ISG15-CHOP2 substrates. Compound 7 inhibited PLpro with Ub-rhodamine and ISG15 substrates with IC$_{50}$ values of 76 and 39 nM, respectively. The corresponding IC$_{50}$ values for 9 with these two substrates were 1.96 µM and 20.2 µM, respectively.

Figures 6A, 6B, 6C:
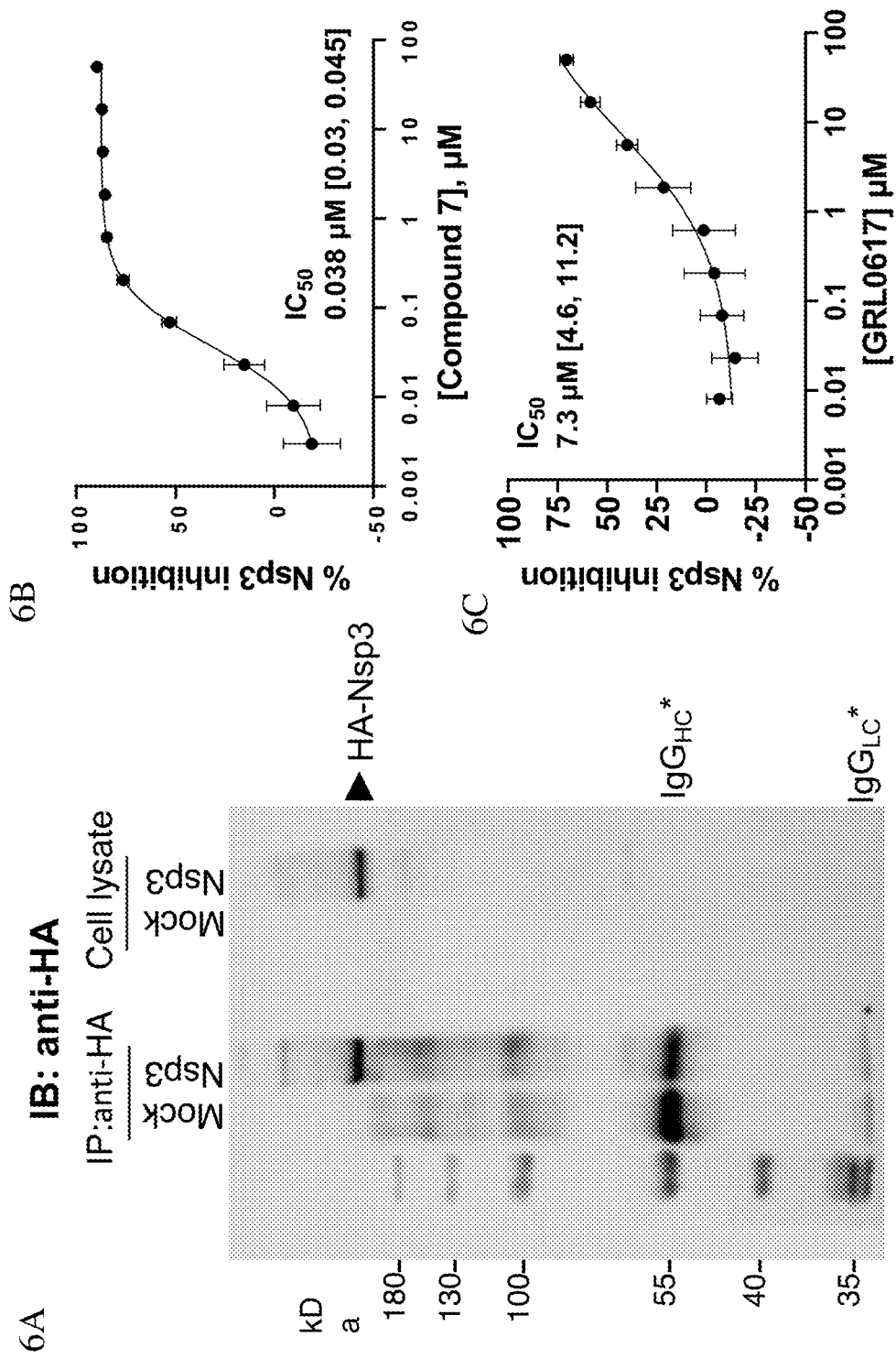
FIGS. 6A-6C. Inhibition of the deISGylase activity of full-length SARS-CoV-2 hemagglutinin (HA)-Nsp3 transiently expressed in HEK293T cells.

Although small molecule-mediated inhibition has been reported for recombinant PLpro domain and for truncated Nsp3, direct inhibition of full-length Nsp3 has not yet been demonstrated. Thus, full-length hemagglutinin (HA)-Nsp3 was expressed in HEK293T cells and the enzyme was purified using anti-HA immunoprecipitation (FIGS. 6A-6C). It has herein been found that compound 7 potently inhibited the deISGylase activity of full-length Nsp3 (IC$_{50}$=0.038 µM). In contrast, GRL0617 showed much weaker inhibition (IC$_{50}$=7.3 µM) under the same assay conditions.

To assess the efficacy of 7 against various SARS-CoV-2 strains, CPE assays were performed with Vero E6 cells infected with the USA-WA1/2020, Delta (B.1.617.2), or Omicron (B.1.1.529) variant (Table 7). Vero cells overexpress the efflux transporter P-glycoprotein (P-gp); thus, assays of 7 in the presence of the P-gp inhibitor CP-100356 were performed. Variant-dependent $EC_{50}$ values of 0.068 µM for USA-WA1/2020, 0.29 µM for Delta, and 0.68 µM for Omicron were observed using a neutral red staining assay. The origin of these differences is unclear, although it is noted there are no characteristic mutations in the PLpro region of Nsp3 from the B.1.617.2 or B.1.1.529 variants relative to USA-WA1/2020.

TABLE 7

Cytopathic effect of compound 7 against three variants of SARS-CoV-2 in Vero E6 cells in the presence of 2 µM CP-100356.

| Strain | $EC_{50}^a$ (µM) | $CC_{50}^b$ (µM) | $SI_{50}^c$ |
|---|---|---|---|
| USA-WA1/2020 | 0.068 | >10 | >150 |
| Delta (B1.617.2) | 0.29 | >10 | >34 |
| Omicron (B1.1.529) | 0.68 | >10 | >34 |

To provide further confirmation of the antiviral activity of compounds in human cells, the compounds were evaluated in virus yield reduction assays using Caco-2 cells. $EC_{90}$ values were measured for 7 in Caco-2 cells infected with the USA-WA1/2020, Delta (B.1.617.2), or Omicron (B.1.1.529) variant (Table 8). In contrast to the cytopathic protection assays performed with Vero 76 cells, the results varied more substantially among strains in this case. The $EC_{90}$ was 0.26 µM for USA-WA1/2020, >10 µM for Delta, and 2.4 µM for Omicron. The reason for the weaker activity against the Delta and Omicron variants is unclear.

TABLE 8

Cytopathic Effect Assay Data for Compound 7 Against Three Variants of SARS-CoV-2 in Caco-2 Cells.

| Strain | $EC_{90}^a$ (µM) | $CC_{50}^b$ (µM) | $SI_{90}^c$ |
|---|---|---|---|
| USA-WA1/2020 | 0.26 | >10 | >38 |
| Delta (B1.617.2) | >10 | >10 | 0 |
| Omicron (B1.1.529) | 2.4 | >10 | >4.2 |

Figures 7A, 7B, 7C, 7D:
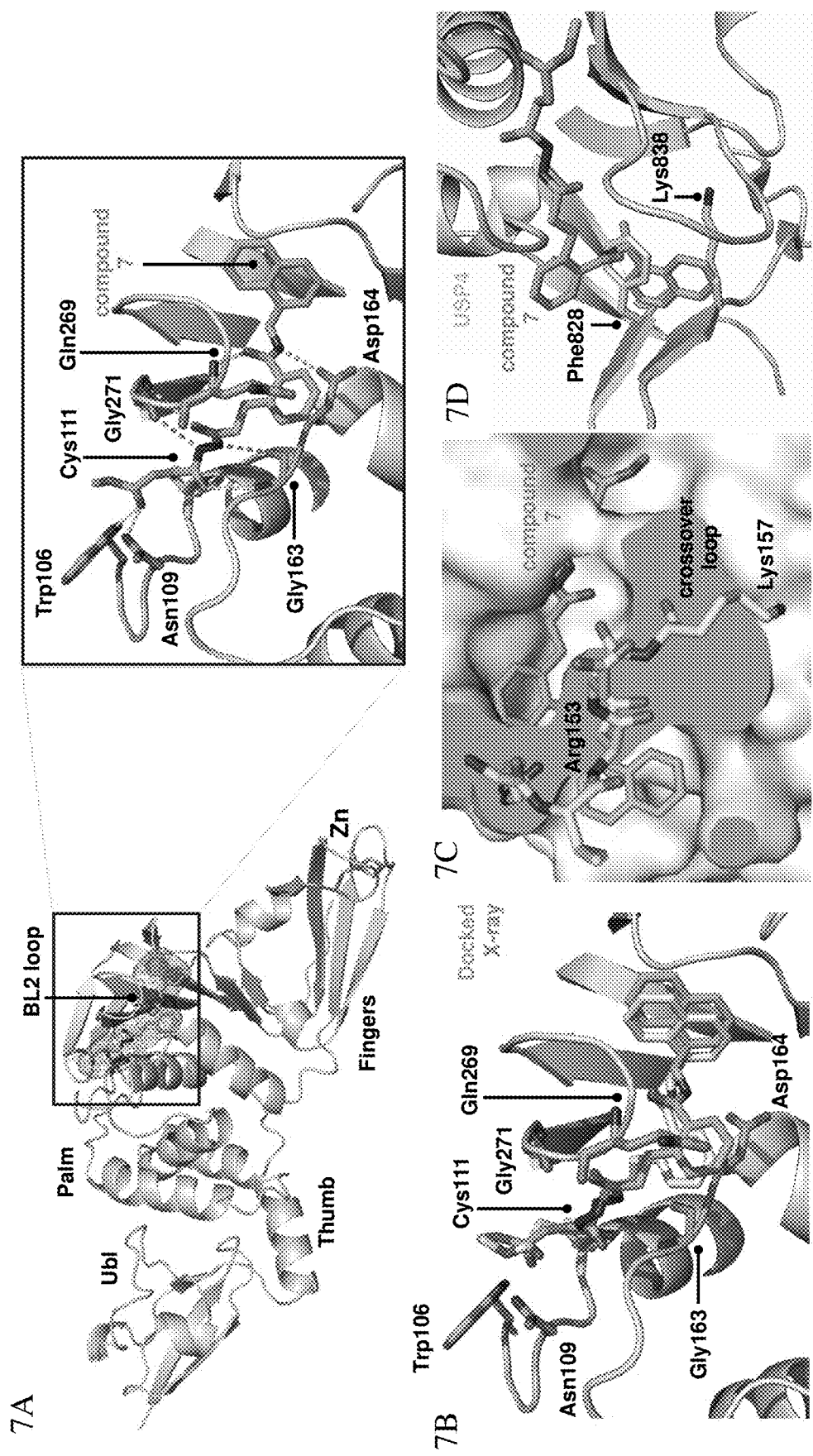
FIGS. 7A-7D. Crystal structure of SARS-CoV-2 PLpro in complex with inhibitor 7.

Following the promising results from in vitro assays and mass spectrometry experiments, the crystal structure of wild-type PLpro in complex with 7 at 3.10 Å resolution was determined. The electron density maps show clear densities for PLpro, Zn cations, and 7, confirming the design concept of this compound and revealing key interactions with PLpro (FIGS. 7A-7D). A covalent bond is present between Sg of Cys111 and the R carbon of the ester of 7 (FIG. 7A). The carbonyl oxygen of the ester accepts hydrogen bonds from the indole side chain of Trp106, like that of the tetrapeptide-based covalent inhibitor VIR251, and from the side chain of Asn109. The N,N'-acetylacetohydrazine moiety was designed to link the electrophile and the naphthylmethylamine core while also hydrogen bonding with residues in the S1-S2 groove. Indeed, the crystal structure revealed that the proximal and distal carbonyl oxygens of the linker interact with the backbone N—H groups of Gly163 and Gly271, and the proximal and distal N—H groups of this moiety participate in hydrogen bonds with the carbonyl backbones of Gly271 and Gly163. As intended, the carbonyl oxygen and N—H group of the amide adjacent to the naphthyl group of 7 are hydrogen bonded with the N—H backbone of Gln269 and the carboxylate side chain of Asp164. Compound 7 makes five main-chain and three side-chain hydrogen bonding interactions in the binding site. In addition, the side chains of Tyr268 and Gln269 interact with 7 similarly to GRL0617. Electron density for the methyl group of the ester of 7 was not visible. It is possible that the ester linkage is flexible and adopts multiple conformations or that it could have been hydrolyzed after covalent bond formation. Notably, the covalently docked pose for 7 agrees closely with the co-crystal structure (FIG. 7B).

The metabolic stability of selected compounds was determined in human, rat, and mouse liver microsomes and the corresponding S9 fractions. Chloroacetamide 9 demonstrated very short half-lives of 7 and 3 minutes in human liver microsomes and S9 fractions, respectively, likely due to the highly reactive electrophile. Non-covalent inhibitor 14 exhibited a half-life of 41 min in human liver microsomes and >60 min in the S9 fraction and conversion of 14 to its covalent counterpart 7 maintained the half-life (50 min in microsomes and 60 min in S9). Analysis of 14 and 7 with MetaSite 6.0.1 (G. Cruciani et al., *J. Med. Chem.*, 48(22), 6970-9, 2005) suggested that successive oxidations of the tolyl methyl of 14 are the predominant metabolic liability, followed by the benzylic methylene. Given that the linker and electrophile replaced the labile methyl group, it is unsurprising that the benzylic methylene is predicted to be the primary site of metabolism for 7. To address the benzylic liability several modifications could be pursued, including substitution of the benzylic position with a heavy atom, such as fluorine or deuterium to increase steric hindrance, or blocking the site of metabolism via replacement of the tolyl methyl with cyclopropyl.

Compound 7 was advanced into a pharmacokinetic study to assess its in vivo exposure. Male ICR mice were dosed with 10 mg/kg (PO) or 3 mg/kg (IV) to obtain a complete picture of the PK/PD profile. Unfortunately, 7 was not orally bioavailable and there was no exposure recorded following PO dosing. The PK parameters following IV dosing were determined. Little exposure was observed and the levels of 7 did not meet the threshold for progression into an in vivo efficacy study.

Numerous research efforts have focused on developing inhibitors of 3CLpro, but relatively few have focused on PLpro inhibition. A predominant reason for the emphasis on 3CLpro as an antiviral target is that there are no structural homologs in the human proteome, whereas PLpro bears structural similarity to human DUBs and deISGylases. However, the present findings demonstrate that covalent inhibition of PLpro is a promising strategy for developing potent and selective therapeutics to combat SARS-CoV-2. Furthermore, the crystal structure of the most promising inhibitor covalently bound to PLpro provides insight that will facilitate the development of next-generation PLpro inhibitors with enhanced pharmacokinetic and pharmacodynamic properties.

While there have been shown and described what are at present considered the preferred embodiments of the invention, those skilled in the art may make various changes and modifications which remain within the scope of the invention defined by the appended claims.

What is claimed is:

1. A compound having the following structure:

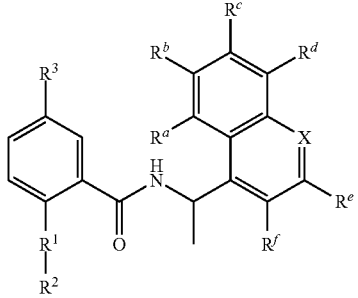
(1)

wherein:

$R^1$ is a linker having the formula —(CH$_2$)$_n$-L$^1$-, wherein L$^1$ contains 1-6 carbon atoms and at least one —NH— linkage and at least one oxygen-containing or sulfur-containing linkage, and n is an integer of 0-3;

$R^2$ is a group having the formula —C(Y)-E, wherein Y is O or S, and E is a hydrocarbon group containing 1-12 carbon atoms and either: (i) at least one carbon-carbon or carbon-nitrogen unsaturated bond or (ii) at least one alkyl halide group;

$R^3$ is selected from the group consisting of H, NR'$_2$, NHC(O)R', and —(CH$_2$)$_p$-T, wherein T contains at least one —NH— linkage; R' is independently selected from H and hydrocarbon groups containing 1-6 carbon atoms; and p is an integer of 0-3;

$R^a$, $R^b$, $R^c$, $R^d$, $R^e$, and $R^f$ are independently selected from the group consisting of H, hydrocarbon groups containing 1-3 carbon atoms, fluorine atom, and chlorine atom;

X is N or CR$^9$, wherein R$^9$ is selected from the group consisting of H, hydrocarbon groups containing 1-3 carbon atoms, fluorine atom, and chlorine atom;

and pharmaceutically acceptable salts thereof.

2. The compound of claim 1, wherein $R^1$ is a linker having the formula —(CH$_2$)$_n$-L$^1$-, wherein L$^1$ contains 1-6 carbon atoms and at least one —NH— linkage and at least one oxygen-containing linkage selected from the group consisting of C(O), SO$_2$, PO$_2$, and hydroxy-containing linkages, and n is an integer of 1-3.

3. The compound of claim 1, wherein $R^1$ contains a hydrazide linkage.

4. The compound of claim 1, wherein $R^2$ is a group having the formula —C(Y)-E, wherein Y is O or S, and E is a hydrocarbon group containing 1-12 carbon atoms and at least one carbon-carbon or carbon-nitrogen unsaturated bond.

5. The compound of claim 4, wherein $R^2$ has the formula —C(Y)—(C≡C)—C(O)O—V, where Y is O or S, and V is a hydrocarbon group containing 1-12 carbon atoms, optionally substituted with one or more F atoms.

6. The compound of claim 5, wherein V is a bulky hydrocarbon group selected from the group consisting of branched alkyl, alkenyl, and alkynyl groups containing 3-6 carbon atoms; and groups of the formula —(CH$_2$)$_r$—U, wherein U is a carbocyclic or heterocyclic group and r is an integer of 0-3.

7. The compound of claim 1, wherein $R^2$ is a group having the formula —C(Y)-E, wherein Y is O or S, and E is a hydrocarbon group containing 1-12 carbon atoms and at least one alkyl halide group.

8. The compound of claim 7, wherein $R^2$ has the formula —C(Y)—(CH$_2$)$_s$—W, wherein W is halogen.

9. The compound of claim 1, wherein $R^3$ is H.

10. The compound of claim 1, wherein $R^3$ is NH$_2$.

11. The compound of claim 1, wherein $R^3$ is NHC(O)R', wherein R' is independently selected from H and hydrocarbon groups containing 1-6 carbon atoms.

12. The compound of claim 1, wherein the compound has the following structure:

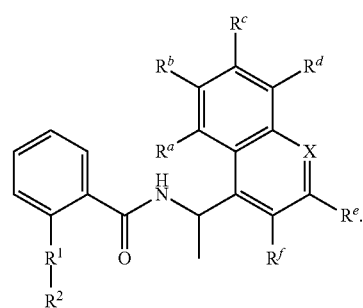
(1a)

13. The compound of claim 1, wherein the compound has the following structure:

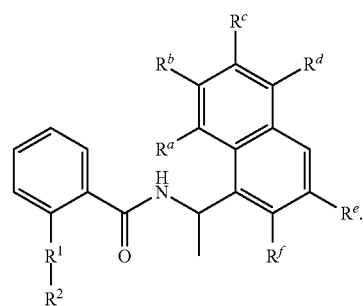
(1b)

14. The compound of claim 1, wherein the compound has the following structure:

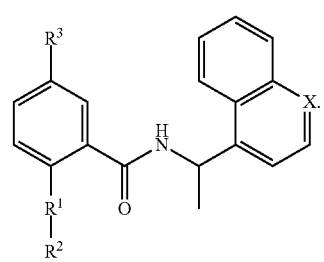
(1c)

15. The compound of claim 1, wherein the compound has the following structure:

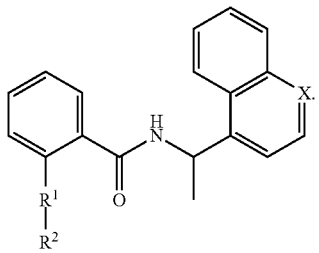

(1d)

16. The compound of claim 1, wherein the compound has the following structure:

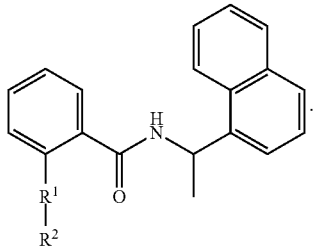

(1e)

17. The compound of claim 16, wherein $R^1$ contains a hydrazide linkage.

18. The compound of claim 16, wherein $R^2$ is a group having the formula —C(Y)-E, wherein Y is O or S, and E is a hydrocarbon group containing 1-12 carbon atoms and at least one carbon-carbon or carbon-nitrogen unsaturated bond.

19. The compound of claim 18, wherein $R^2$ has the formula —C(Y)—(C≡C)—C(O)O—V, where Y is O or S, and V is a hydrocarbon group containing 1-12 carbon atoms, optionally substituted with one or more F atoms.

20. The compound of claim 19, wherein V is a bulky hydrocarbon group selected from the group consisting of branched alkyl, alkenyl, and alkynyl groups containing 3-6 carbon atoms; and groups of the formula —(CH$_2$)$_r$—U, wherein U is a carbocyclic or heterocyclic group and r is an integer of 0-3.

21. The compound of claim 16, wherein $R^2$ is a group having the formula —C(Y)-E, wherein Y is O or S, and E is a hydrocarbon group containing 1-12 carbon atoms and at least one alkyl halide group.

22. The compound of claim 21, wherein $R^2$ has the formula —C(Y)—(CH$_2$)$_s$—W, wherein W is halogen.

23. A pharmaceutical composition comprising a compound of Formula (1) and a pharmaceutically acceptable carrier.

24. A method of inhibiting papain-like protease (PLpro) activity in a subject, the method comprising administering a therapeutically effective dosage of a compound of Formula (1) to the subject to result in inhibition of PLpro activity in the subject.

25. The method of claim 24, wherein the PLpro activity is mediated by a coronavirus PLpro.

26. A method of treating coronavirus infection in a subject, the method comprising administering a therapeutically effective dosage of a compound of Formula (1) to the subject to result in inhibition or prevention of one or more coronavirus symptoms in the subject.

* * * * *